US008241295B2

(12) United States Patent
Wolf, II

(10) Patent No.: US 8,241,295 B2
(45) Date of Patent: Aug. 14, 2012

(54) APPARATUS AND METHOD FOR THE DISPENSING OF BONE CEMENT

(76) Inventor: Erich W. Wolf, II, Lake Charles, LA (US)

( * ) Notice: Subject to any disclaimer, the term of this patent is extended or adjusted under 35 U.S.C. 154(b) by 1177 days.

(21) Appl. No.: 12/075,652

(22) Filed: Mar. 13, 2008

(65) Prior Publication Data

US 2009/0062808 A1 Mar. 5, 2009

Related U.S. Application Data

(60) Provisional application No. 60/967,698, filed on Sep. 5, 2007.

(51) Int. Cl.
*A61B 17/56* (2006.01)

(52) U.S. Cl. ............................... 606/92; 606/93; 606/94

(58) Field of Classification Search ............... 623/23.62, 623/908; 606/92, 93, 94, 95
See application file for complete search history.

(56) References Cited

U.S. PATENT DOCUMENTS 5,269,146 A 12/1993 Kerner
5,975,856 A 11/1999 Welle
6,506,494 B2 1/2003 Brandys et al.
6,945,638 B2 9/2005 Teung et al.
7,235,735 B2 6/2007 Venkatasubramanian
8,001,794 B2 * 8/2011 Windisch ......................... 62/3.5
2003/0221717 A1 12/2003 Dessel
2006/0151021 A1 7/2006 Stark
2006/0288708 A1 12/2006 Maltezos et al.
2007/0191858 A1 8/2007 Truckai et al.
2007/0194465 A1 8/2007 Dai et al.
2007/0199333 A1 8/2007 Windisch
2008/0039855 A1 * 2/2008 Lambert ......................... 606/93
2008/0243129 A1 * 10/2008 Steffen et al. ................... 606/93
2009/0204120 A1 * 8/2009 Trosken et al. ................. 606/93

FOREIGN PATENT DOCUMENTS

WO WO2005053510 6/2005
WO WO2005109535 11/2005
WO WO2006103410 10/2006
WO WO2006107007 10/2006

* cited by examiner

*Primary Examiner* — William H Matthews
*Assistant Examiner* — Suba Ganesan
(74) *Attorney, Agent, or Firm* — Schultz & Associates, P.C.

(57) ABSTRACT

Apparatus and method to dispense PMMA bone cement including a temperature controller, a disposable cement cartridge and a means for extracting cement from the cement cartridge so that the temperature of the extracted cement is first cooled to discourage polymerization and to prolong working time, then warmed so as to control viscosity of the cement flowing into the desired bone repair location. A first embodiment includes a spiral cement cartridge along with a means for extracting cement therefrom. A second embodiment includes a linear disposable cement cartridge along with a means for extracting cement therefrom. A color matching mechanism identifies cement temperature and viscosity during dispensation. A manual cement dispensing method includes a calibrated hand crank mechanism for causing calibrated delivery of cement. An automatic cement dispensing method uses a stepper motor and computer programmed means for causing calibrated flow of cement.

31 Claims, 24 Drawing Sheets

300 315 312 307 313 313 302 307 303 308 311 304 306 316

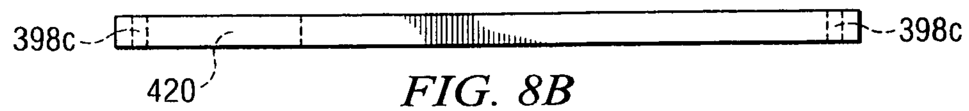
FIG. 8B
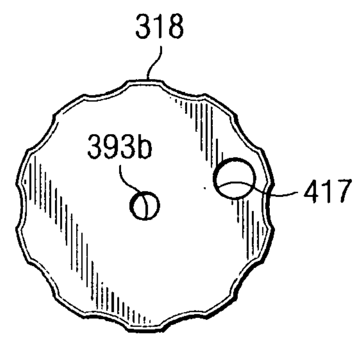
FIG. 8C
393b 417
318
FIG. 8D
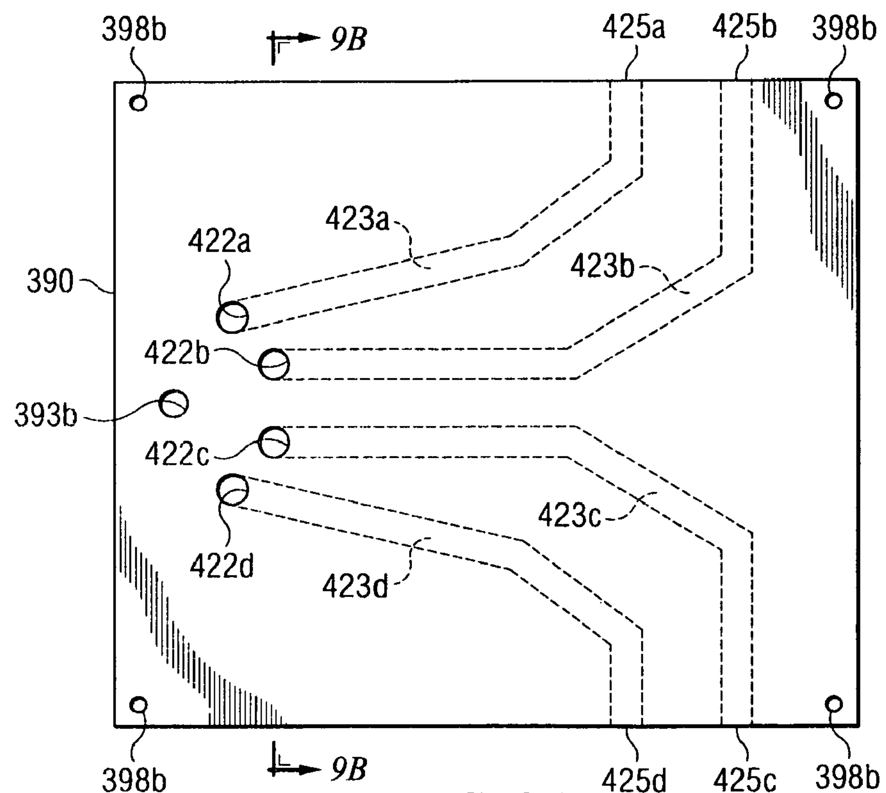
FIG. 9A

APPARATUS AND METHOD FOR THE DISPENSING OF BONE CEMENT

This application claims priority to U.S. provisional patent application No. 60/967,698 filed on Sep. 5, 2007.

TECHNICAL FIELD OF THE INVENTION

The present invention relates to the controlled delivery of PMMA cement and more specifically to a cement dispenser device for the controlled delivery of bone cement in orthopedic surgical operations.

BACKGROUND OF THE INVENTION

Poly-methyl-methacrylate (PMMA) bone cement has been in use since about 1960 for hip replacement surgery and not long thereafter came into use for percutaneous vertebroplasty, the latter being a palliative procedure requiring the injection of bone cement into the vertebral body at the cervical, thoracic or lumbar locations. The indications for percutaneous vertebroplasty are severe osteoporosis with vertebral compression fractures and vertebral haemangiomas and possibly patients with vertebral tumors. PMMA cement is manually injected into the vertebral body, the cement usually containing a high concentration of zirconium dioxide to allow for X-ray fluoroscopy. The cement permeates the vertebral body hardening and stabilizing the bony structure, the surgical procedure intending to stabilize the affected site and provide relief from significant pain.

PMMA is dough-like cement that gradually hardens into a solid material with good biocompatibility. The preparation of PMMA bone cement requires the combination of two components: a solid powder and a liquid monomer. The cement becomes progressively viscous as polymerization to poly-methyl-methacrylate proceeds at a rate governed by the Arrhenius equation. Specific clinical applications such as vertebral fracture augmentation (e.g. kyphoplasty, vertebroplasty, arcuplasty) demand an optimal range of viscosity. Upon mixing the two components, the latency to achieve usable viscosity is dependent on the ambient temperature. In clinical use it is often difficult to accurately anticipate the appropriate time for mixing of the PMMA. Consequently, it is frequent to wait for adequate polymerization before proceeding. Conversely, occasionally the PMMA will be too viscous to apply and will need to be discarded. A need exists in the art to adequately control the polymerization process and the viscosity of delivered PMMA in clinical orthopedic applications.

The present invention incorporates a solid-state Peltier junction with a PMMA reservoir on the cold side to prevent premature polymerization. As the PMMA is needed it is passed over the heated (opposite) side to provide adequate activation energy to ensure adequate polymerization as the PMMA exits the apparatus. A roller pump is integrated into the device.

Arrhenius equation may be utilized to predict cement activation and viscosity. As known in the art, Arrhenius equation is an expression that shows the dependence of the rate constant k of chemical reactions on the temperature T (in Kelvin) and activation energy Ea, according to:

$$k=Ae^{-E_\alpha/RT}.$$

where A is the pre-exponential factor or simply the prefactor and R is the gas constant. The units of the pre-exponential factor are identical to those of the rate constant and will vary depending on the order of the reaction. If the reaction is first order it has the units $s^{-1}$, and for that reason it is often called the frequency factor or attempt frequency of the reaction. When the activation energy is given in molecular units, instead of molar units, e.g. joules per molecule instead of joules per mol, the Boltzmann constant is used instead of the gas constant. It can be seen that either increasing the temperature or decreasing the activation energy (for example through the use of catalysts) will result in an increase in rate of reaction.

Given the small temperature range in which kinetic studies are carried, it is reasonable to approximate the activation energy as being independent of temperature. Similarly, under a wide range of practical conditions, the weak temperature dependence of the pre-exponential factor is negligible compared to the temperature dependence of the exponential factor, $\exp(-E_\alpha/RT)$; except in the case of "barrierless" diffusion-limited reactions, in which case the pre-exponential factor is dominant and is directly observable.

When a reaction has a rate constant which obeys the Arrhenius equation, a plot of ln(k) versus 1/T gives a straight line, whose slope and intercept can be used to determine $E_\alpha$ and A. This procedure has become so common in the art of chemical kinetics that practitioners often use it to define the activation energy for a reaction. That is the activation energy is defined to be (−R) times the slope of a plot of ln(k) vs. (1/T) at constant pressure P:

$$E_a \equiv -R\left(\frac{\partial \ln k}{\partial(1/T)}\right)_P$$

Once the activation energy Ea is determined for a given reaction involving PMMA cement, the viscosity may be predicted as a function of temperature and reaction time as known in the art. Furthermore, PMMA cement may be mixed with a chemical additive which predictably changes color with temperature as shown by D. C. Smith and M. E. D Bains, J. D. Res, Vol 35, No. 1, p 16-24. A bone cement dispensing device that controls PMMA cement temperature and uses a color based temperature indicator would be useful for delivering PMMA cement at a desired viscosity, temperature and polymerization rate to the desired bone location for proper setup. It is the objective of the present invention to provide such a bone cement dispensing device.

SUMMARY OF THE INVENTION

The present invention is an apparatus and method conceived for delivering PMMA bone cement in a procedure to attach bone or fill a bone cavity. A first embodiment bone cement dispenser utilizes a spiral shaped cement cartridge and a spiral shaped cement extractor. A second embodiment bone cement dispenser utilizes a rectangular shaped cement cartridge and a rectangular shaped cement extractor. These embodiments have the common inventive feature of cooling the cement in the cement cartridge and heating the cement as it is dispensed.

A first embodiment bone cement dispenser is comprised of a housing with a bone cement dispensing mechanism contained therein and a crank attached to the bone cement dispensing mechanism to effect the delivery of bone cement. Bone cement is dispensed through Luer-lock ports to cement hoses which are placed in proximity to the bone or vertebra to be cemented. A handle is attached to the housing for holding the dispenser while turning the crank. An output selector is included on the bone cement dispenser to select one of four output cement hoses. A viewing port indicates the color of cooled cement which may be compared to a color chart placed on the housing, the color chart associating cement color to a temperature and viscosity of cement.

Dispensing mechanism of first embodiment bone cement dispenser is comprised of a cement extractor placed above a cement temperature controller, the cement cartridge being inserted. The cement extractor includes a cement extraction plate, an extractor disc placed inside the cement extraction plate and made to rotate about an axle shaft inserted through the extraction plate. The cement extraction plate has a spiral ball guide attached for controlling the movement of ball along a spiral path, the ball being held in a radial ball slot in the extractor disc. The crank is in contact with an extractor disc so as to effect rotational motion of the extractor disc. The cement extraction plate, extractor disc, extractor ball, crank and spiral ball guide are assembled to form a cement extractor.

The cement temperature controller is comprised of a cold plate, a Peltier plate and a hot plate, the Peltier plate being in thermal contact with the cold plate and hot plate and further being configured to transfer heat from the cold plate to the hot plate when a voltage is applied thereto. Cavities are made in the cold plate and in the hot plate to transfer cement from the cement cartridge to a selectable output hose. The output selector is positioned in the Peltier plate and allows connection between cold plate cavities and hot plate cavities.

The cement extractor is attached by a hinge mechanism to the cement temperature controller, the two being opened and closed to effect the placement of a spiral shaped cement cartridge there between. The cement cartridge and cement contained therein is cooled by the cold plate in operation.

In use the crank is rotated, causing the ball within the cement extractor to press on the cement cartridge and extract cement therefrom. Extracted cement flows from the upper surface of the cold plate to a cavity on the lower surface of the cold plate. Cement continues to flow through the output selector and then through a cavity inside the hot plate where the cement is warmed to a temperature consistent with the desired viscosity and setup time for the procedure. Cement exits the hot plate and is dispensed through output cement hoses.

A second embodiment bone cement dispenser is comprised of a housing with a bone cement dispensing mechanism contained therein and a crank attached to the bone cement dispensing mechanism to effect the delivery of bone cement. Bone cement is dispensed through Luer-lock ports to cement hoses which are placed in proximity to the bone or vertebra to be cemented. A handle is attached to the housing for holding the dispenser while turning the crank.

An output selector is included on the bone cement dispenser to select one of four output cement hoses. A viewing port indicates the color of cooled cement which may be compared to a color chart placed on the housing, the color chart associating cement color to a temperature and viscosity of cement.

The dispensing mechanism of a second embodiment bone cement dispenser is comprised of a cement extractor placed above a cement temperature controller, the cement cartridge being inserted there between. The cement extractor includes a cement extraction press attached to a linear slide which translates according to the motion of the crank. The cement extraction press has a cylindrical protrusion for pressing cement out of a rectangular shaped cement cartridge. The cement extraction plate, extractor press, cylindrical protrusion, and crank are assembled to form a cement extractor.

The cement temperature controller is comprised of a cold plate, a Peltier plate and a hot plate, the Peltier plate being in thermal contact with the cold plate and hot plate and further being configured to transfer heat from the cold plate to the hot plate when a voltage is applied thereto. Cavities are made in the cold plate and in the hot plate to transfer cement from the cement cartridge to a selectable output hose. The output selector is positioned in the Peltier plate and allows connection between cold plate cavities and hot plate cavities.

The cement extractor is attached by a hinge mechanism to the cement temperature controller, the two being opened and closed to effect the placement of a rectangular shaped cement cartridge there between. The cement cartridge and cement contained therein is cooled by the cold plate in operation.

In use the crank is rotated, causing the cylindrical protrusion within the cement extractor press to press on the cement cartridge and extract cement therefrom. Extracted cement flows from the upper surface of the cold plate to a cavity on the lower surface of the cold plate. Cement continues to flow through the output selector and then through a cavity inside the hot plate where the cement is warmed to a temperature consistent with the desired viscosity and setup time for the procedure. Cement exits the hot plate and is dispensed through output cement hoses.

The present invention is not limited to be a handheld device or manual device, embodiments conceived to automate the bone cement dispensing process. In an embodiment disclosed herein, the bone cement dispenser is attached to a table with a motor utilized as a rotational drive in place of the previously described crank. The motor may be controlled by manual settings or by programmable means to effect the dispensing of bone cement.

BRIEF DESCRIPTION OF THE DRAWINGS

For a more complete understanding of the exemplary embodiments herein, and for further details and advantages thereof, reference is now made to the following Detailed Description taken in conjunction with the accompanying drawings, in which:

FIGS. 8A, 8B, 8C and 8D are top and side view drawings of the Peltier plate and output selector disc of the first exemplary embodiment.

FIGS. 9A, 9B and 9C are top, side and bottom view drawings, respectively, of the hot plate of the first exemplary embodiment.

DETAILED DESCRIPTION

The present invention is described in the context of a preferred embodiment and other exemplary embodiments. The following description of the preferred embodiment is not intended to limit the application of the inventive concepts but merely provide a concrete example of the inventive concept especially related to the application of bone cement in orthopedic surgery. Other situations may be conceived wherein a temperature controlled and prescribed flow of PMMA cement is applicable and useful to the art.

Figure 1A:
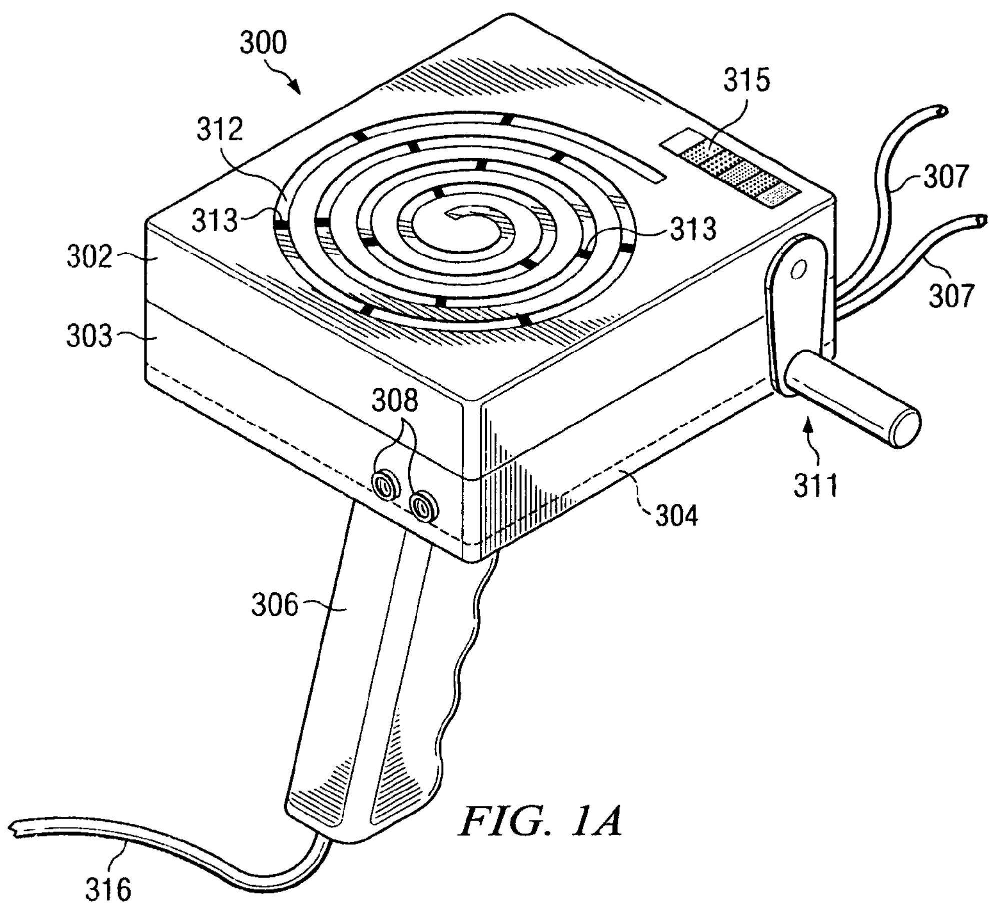
FIG. 1A is a front view isometric drawing of a first exemplary embodiment of a handheld bone cement dispenser.

Referring to FIG. 1A, a first exemplary embodiment of a bone cement dispenser 300 commensurate with the present invention is shown. Bone cement dispenser 300 has an upper housing cover 302 rotatably attached to a lower housing cover 303 which is further attached to a lower housing base 304. A handle 306 is attached to lower housing base 304 so that bone cement dispenser 300 may be held firmly by hand while in operation. Furthermore, a set of four Luer-lock ports 308 are fixed to lower housing cover 303 to which a set of outlet hoses 307 are attached. Outlet hoses 307 provide a path for cement to flow from bone cement dispenser 300 to the point of operation, for example, a human vertebra. Outlet hoses 307 are made of clear plastic in the first exemplary embodiment. Bone cement is stored in a disposable cement cartridge located within bone cement dispenser 300.

A crank 311 is rotatably attached through upper housing cover 302 to a temperature controlled cement dispensing mechanism contained inside bone cement dispenser 300. An indicator 312 with a marked set of graticules 313 appears on the top side of housing cover 302, preferably with a transparent surface showing a marker on the temperature controlled cement dispensing mechanism and useful for indicating a quantity of cement dispensed. Color chart 315 is placed on the top surface of housing cover 302 for indicating cement viscosity by color comparison with dispensed cement. Electrical cable 316 is attached through handle 306 to the temperature controlled cement dispensing mechanism. The cement cartridge and temperature controlled cement dispenser mechanism will be explained further below.

Figure 1B:
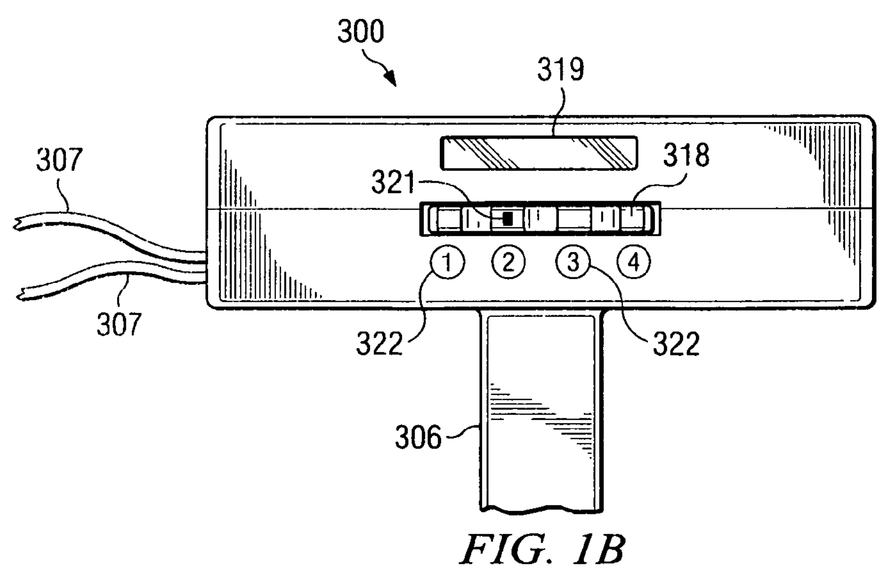
FIG. 1B is a rear view of the first exemplary embodiment of a handheld bone cement dispenser.

A shown in FIG. 1B bone cement dispenser 300 has a rotatable output selector 318 which is a round disc rotating between selectable positions 322 and having indicator 321 indicating the current selector position. Cement dispenser 300 may have viewing port 319 for viewing the color of the cement as it is dispensed.

Figure 2:
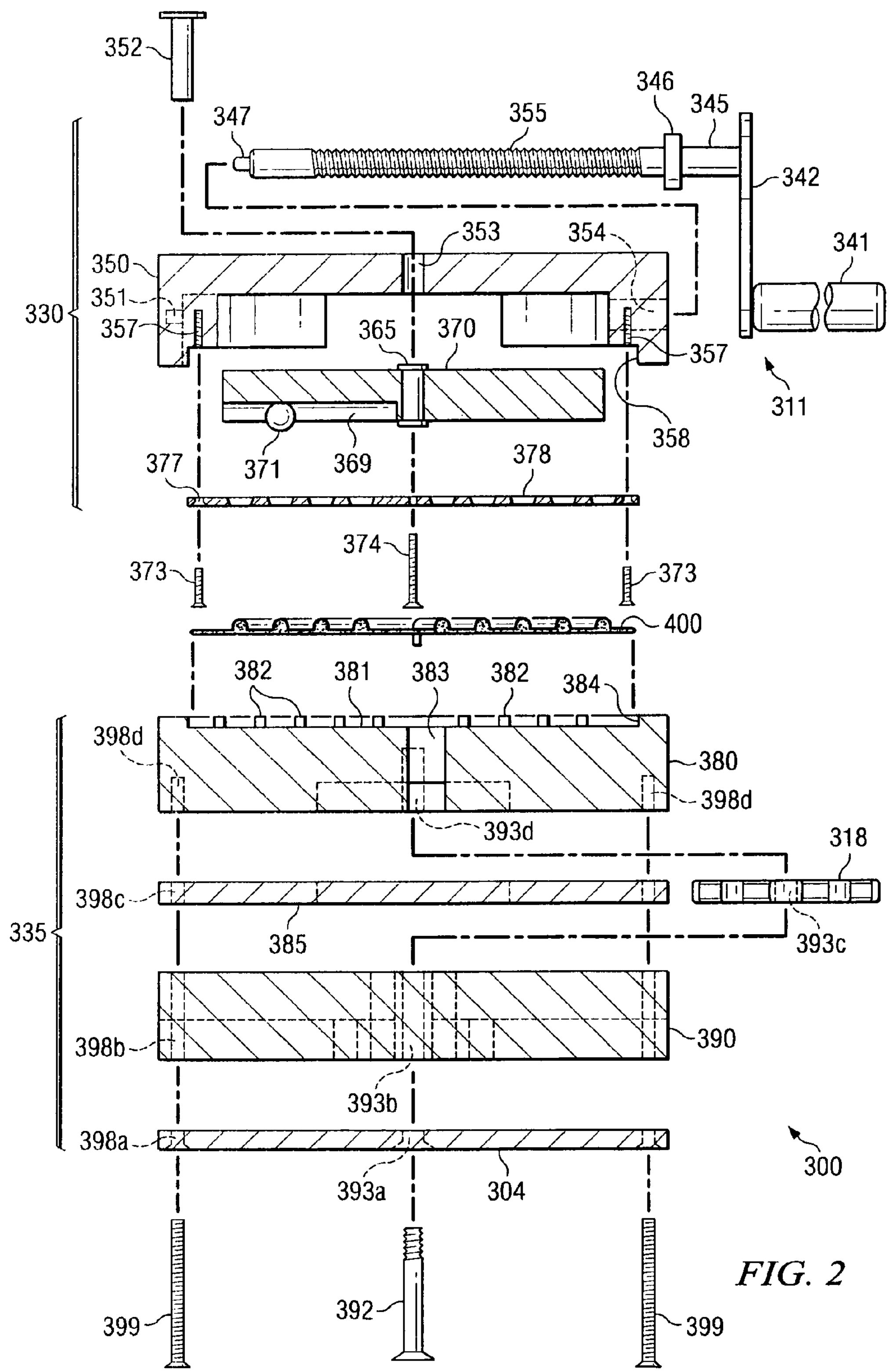
FIG. 2 is an exploded cross-sectional view of the first exemplary embodiment of the cement dispensing mechanism.
Figure 3A:
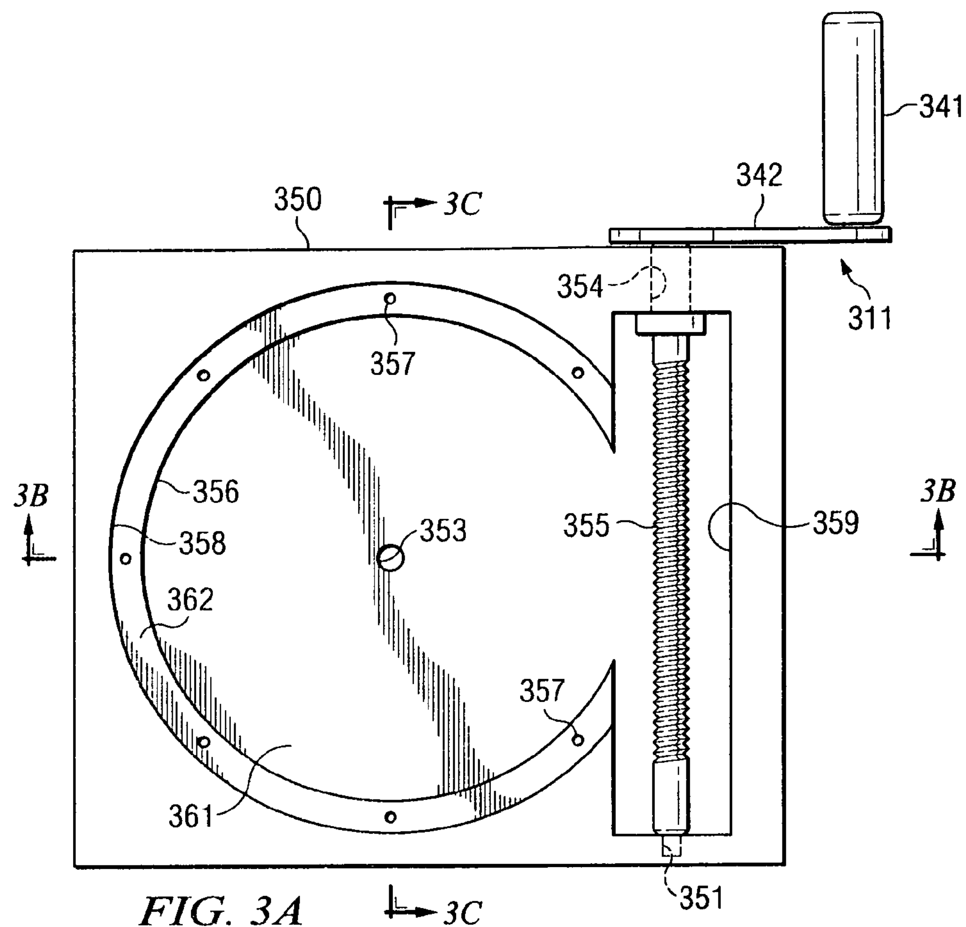
FIGS. 3A, 3B and 3C are top and side view drawings of the cement extractor plate of the first exemplary embodiment.
Figure 3B:
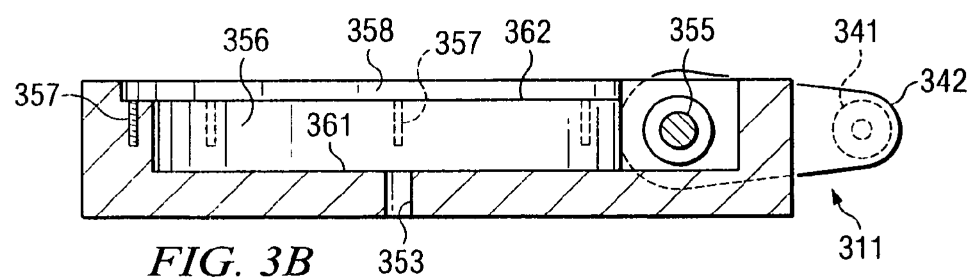
Figure 3C:
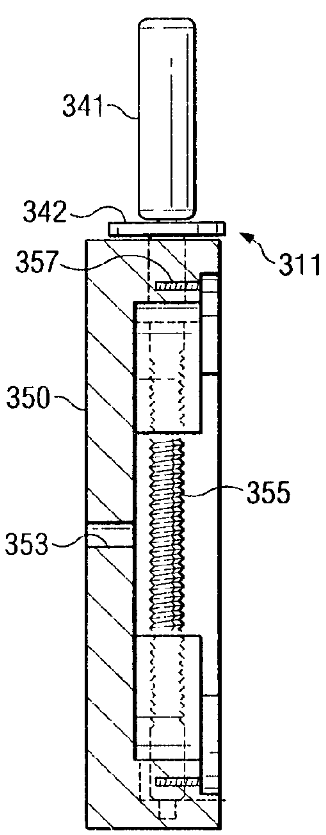

FIG. 2 is a cross-sectional drawing of bone cement dispenser 300 showing the temperature controlled cement dispensing mechanism which comprises a cement extractor assembly 330 and a cement temperature controller 335. The top of bone cement dispenser 300 is near the top of the drawing, the bottom being near the bottom of the drawing so that upper surfaces face the top and lower surfaces face the bottom. Housing base 304 is attached to the bottom of cement temperature controller 335, lower housing cover 303 (shown in FIG. 1) being attached thereto and upper housing cover 302 covering cement extractor assembly 330.

Cement extractor assembly 330 comprises cement extractor plate 350, extractor disc 370, extractor ball 371, spiral ball guide 378, and crank 311. Crank 311 has threaded shaft 355 with smoothed ends, end shaft 347 and shoulder 345, and crank arm 342 attached to threaded shaft 355 and to handle 341. Referring to FIGS. 2, 3*a*, 3*b* and 3*c*, cement extractor plate 350 is a solid plate having a cylindrical cavity 361 with cavity walls 356 and a guide surface 362 with guide wall 358 and threaded holes 357 in guide surface 362. A central hole 353 is drilled through cylindrical cavity 361 to the upper surface of cement extractor plate 350. Cylindrical cavity 361 adjoins a rectangular cavity 359 having hole 354 on one end and hole 351 on the other end. Crank 311 is inserted through hole 354 in cement extractor plate 350 so that end shaft 347 is fixed in end hole 351 but with sufficient clearance to allow rotation. A collar 346 is secured on shoulder 345 to hold crank 311 in place while allowing free rotation of crank 311.

Figure 4A:
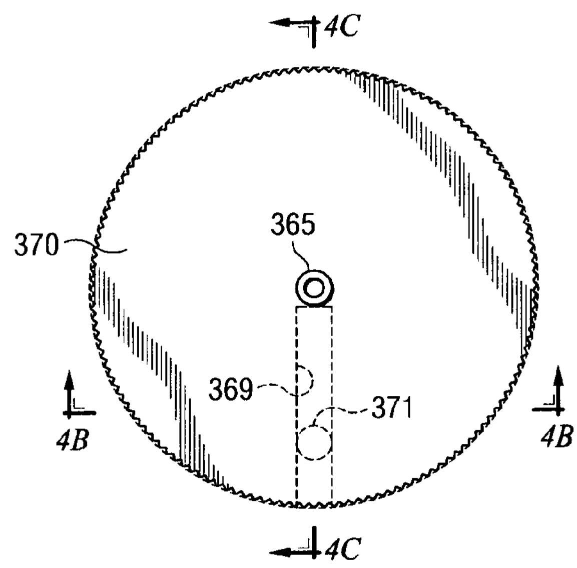
FIGS. 4A, 4B and 4C are top and side view drawings of the extractor disc of the first exemplary embodiment.
Figure 4B:
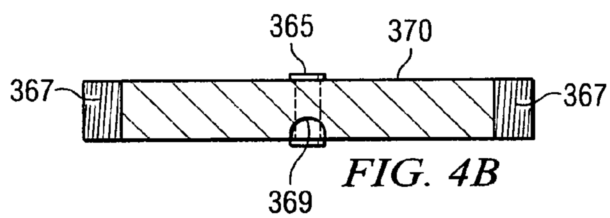
Figure 4C:
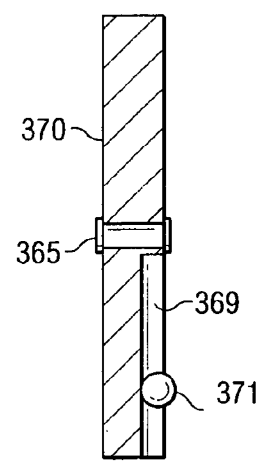

Extractor disc 370 has a diameter similar to that of cylindrical cavity 361 and is positioned inside cylindrical cavity 361. FIGS. 4*a*, 4*b* and 4*c* show a more detailed view of extractor disc 370 which is comprised of a cylindrical solid having a bearing assembly 365 inserted through its center axis allowing for rotation about the center axis. Extractor disc 370 has a linear ball slide 369 along one radius. Extractor ball 371 rolls along the radius with approximately 30% of the ball's surface protruding from ball slide 369. Threads on the outer edge surface 367 are in contact with threaded shaft 355.

Figure 5A:
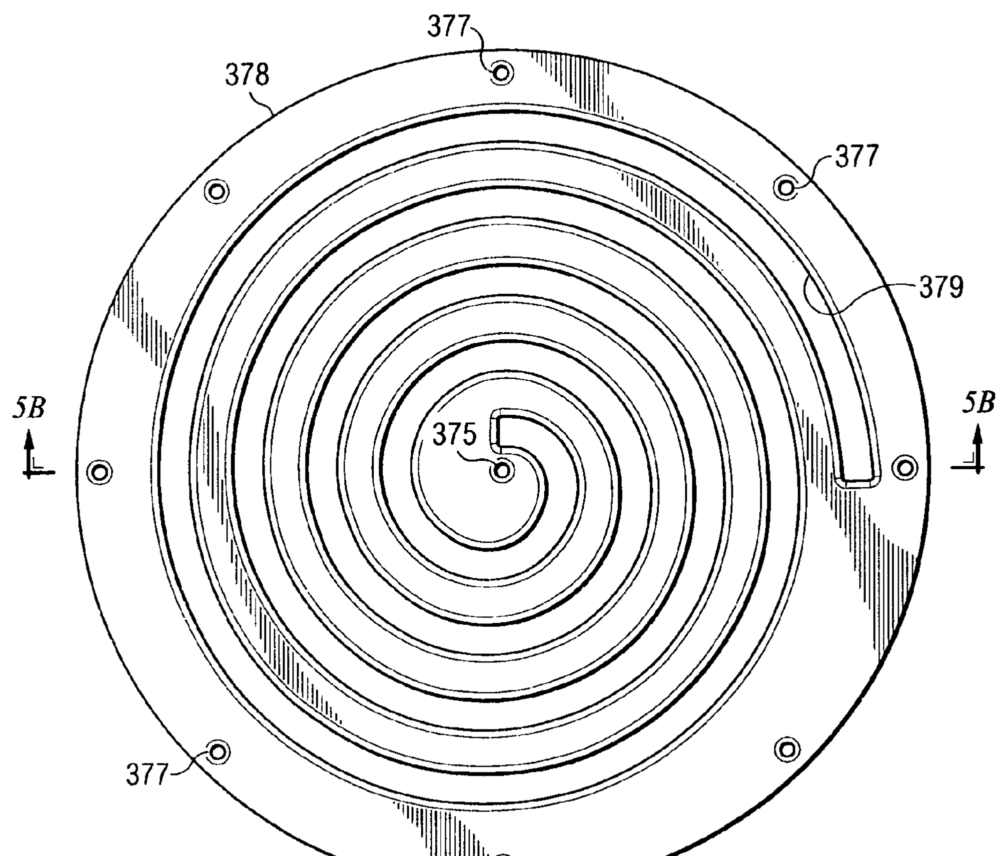
FIGS. 5A and 5B are top and side view drawings of the spiral shaped ball guide of the first exemplary embodiment.
Figure 5B:
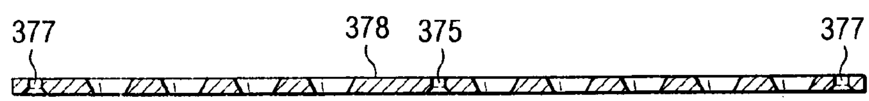

Spiral ball guide 378 is explained with the aid of FIGS. 2, 5*a* and 5*b*. Spiral ball guide 378 is attached to guide surface 362 with a set of screws 373 positioned through a set of holes 377 and into threaded holes 357. Axle screw 374 is inserted through center hole 375 into an upper axle shaft 352 which itself is inserted through the upper surface of cement extractor plate 350. Upper axle shaft 352 further extends through bearing assembly 365 so that spiral ball guide 378 and extractor disc 370 are attached to cement extractor plate 350 to form a single unit with extractor disc 370 rotating on axle shaft 352 with the aid of bearing assembly 365.

Spiral ball guide 378 has a spiral shaped guide 379 extending from the outer radius to near the central point at center hole 375. Extractor ball 371 is positioned inside spiral guide 379 protruding through the lower surface of spiral ball guide 378.

Cement temperature controller 335 is comprised of a cold plate 380, Peltier junction plate 385, hot plate 390 and housing base 304 connected together by a set of assembly screws 399. Peltier junction plate 385 separates cold plate 380 in a first temperature controlled region from hot plate 390 in a second temperature controlled region. Cement temperature controller 335 further comprising an output selector 318 held in place between cold plate 380 and hot plate 390 by a threaded selector shaft 392.

Figure 7A:
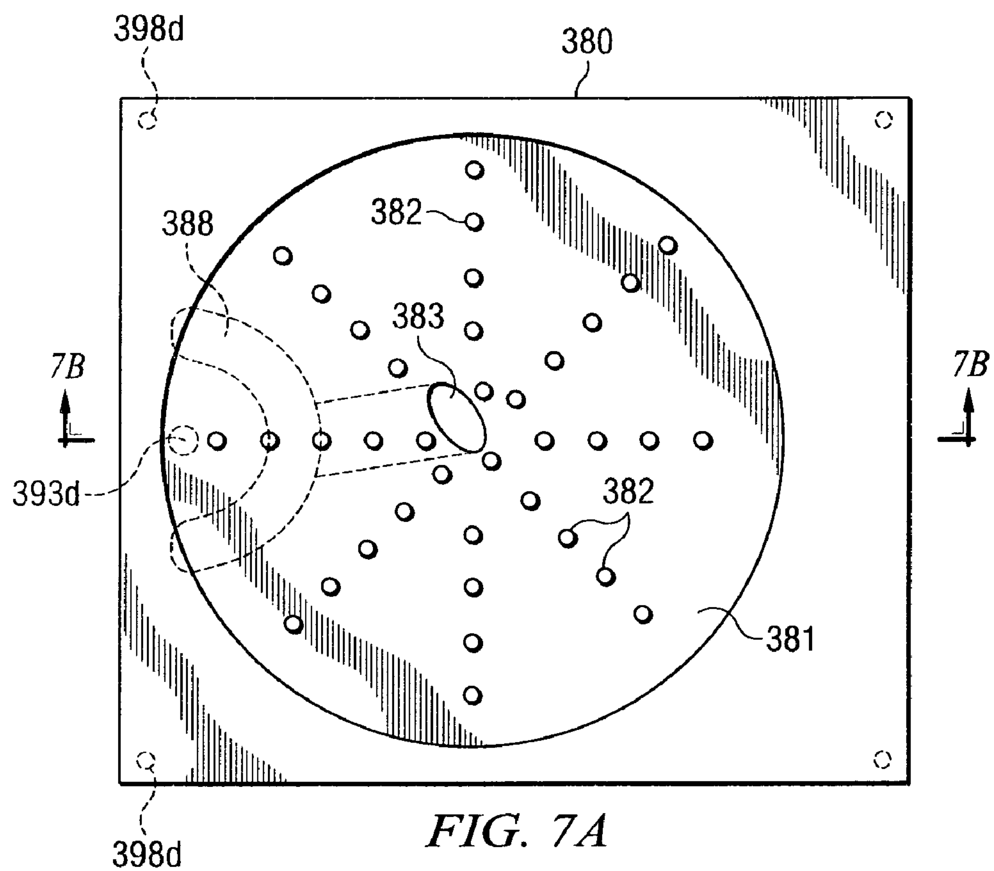
FIGS. 7A, 7B and 7C are top, side and bottom view drawings, respectively, of the cold plate of the first exemplary embodiment.
Figure 7B:
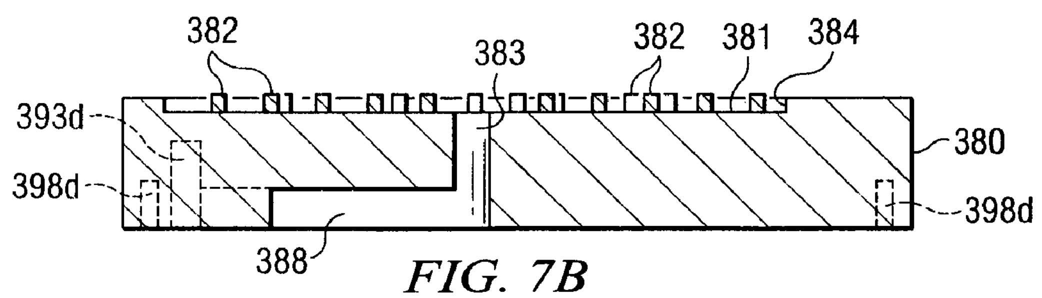
Figure 7C:
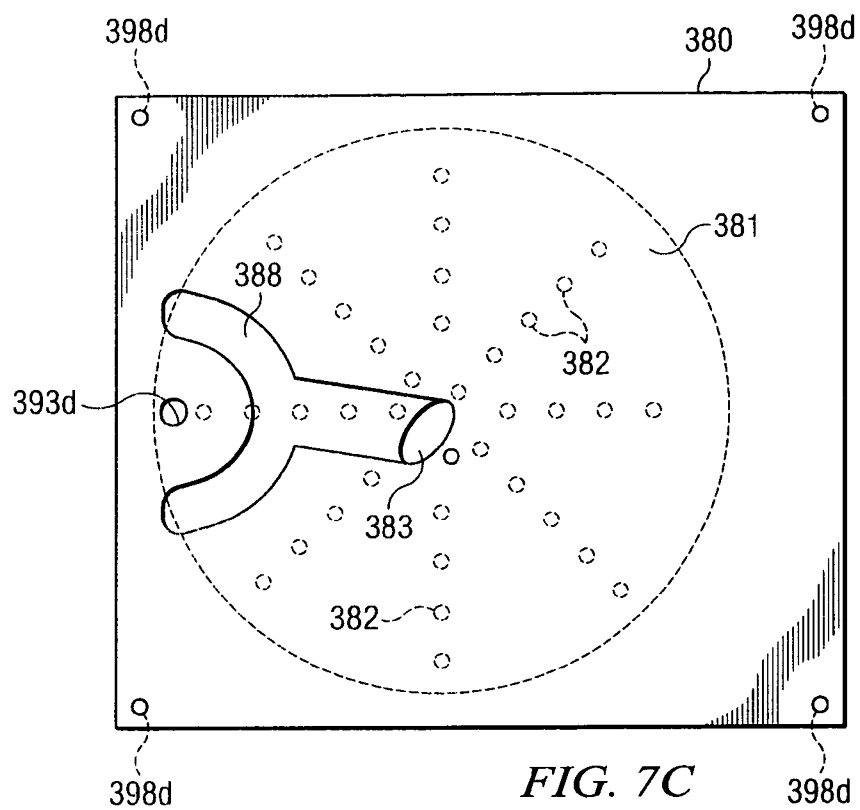

Cold plate 380 is further explained using FIG. 2 in conjunction with FIGS. 7A and 7B wherein cold plate 380 is a rectangular solid with a cartridge receiving area 381 formed as a shallow cylindrical hollow in its upper surface defined by cylindrical wall 384 and having approximate depth of 2 mm. A set of standoff pins 382 is attached on the upper surface inside cartridge receiving area 381 protruding upward from said upper surface. Near the center of cartridge receiving area 381 a hole forming a cement receiver 383 extends from the upper surface to the lower surface. A cavity forming an upper cement channel 388 having a semicircular channel shape on one end and a linear channel shape to the opposite end is made into the lower surface of cold plate 380 so that cement receiver 383 extends into upper cement channel 388. Cold plate 380 has a hole 393*d* drilled through from the upper to the lower surface and a set of threaded holes 398*d* near each corner tapped approximately halfway up from the lower surface.

Peltier junction plate 385 is a thermoelectric device typically made of a stacked series of semiconductor thermocouple elements. Each thermocouple element is made of N-type and P-type semiconductor pieces bonded together. A voltage applied across each element in series causes heat to be transferred from one surface to the other, thereby forming a heat pump which transfers heat from the upper surface in thermal contact with cold plate 380 to the lower surface in thermal contact with hot plate 390. A thermally conductive paste is used to thermally bond the surfaces together.

Figure 8A:
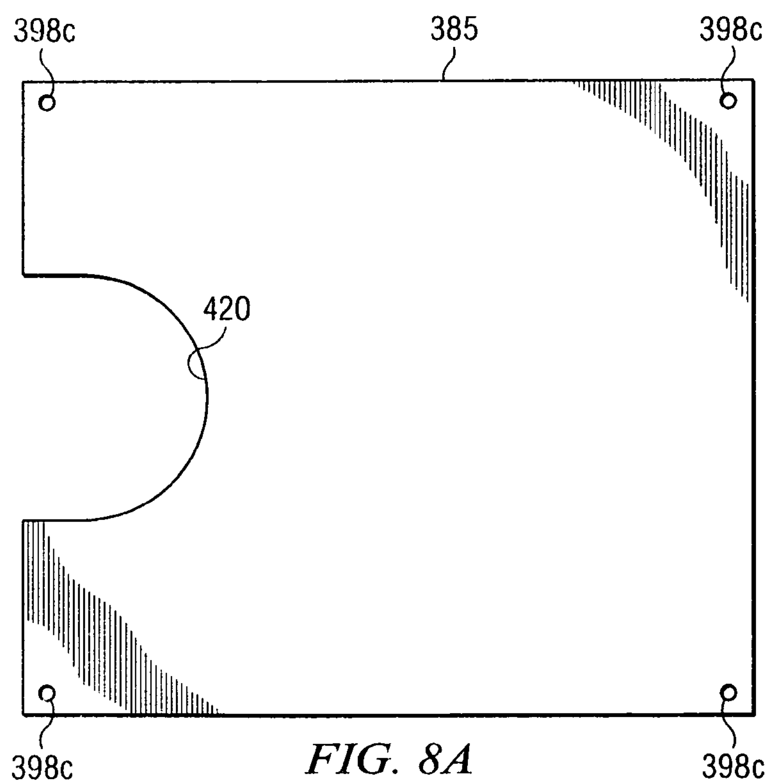

FIG. 8 shows detail of Peltier plate 385 wherein a semicircular notch 420 is cut through plate 385 on one end so that when assembled between the cold and hot plates, a cavity is formed there between to receive output selector 318. A set of holes 398*c* are drilled through Peltier plate 385 near its corners. Output selector 318 has an axis hole 393*b* at its center and a transit hole 417 off center, both holes being drilled through from upper to lower surfaces.

Figure 9B:
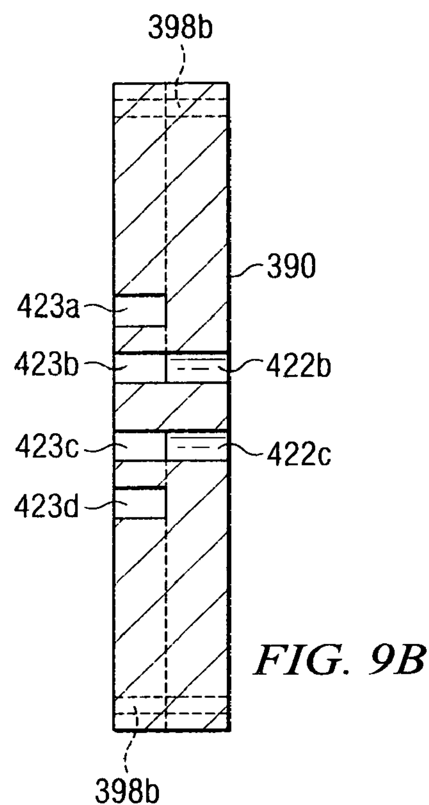
Figure 9C:
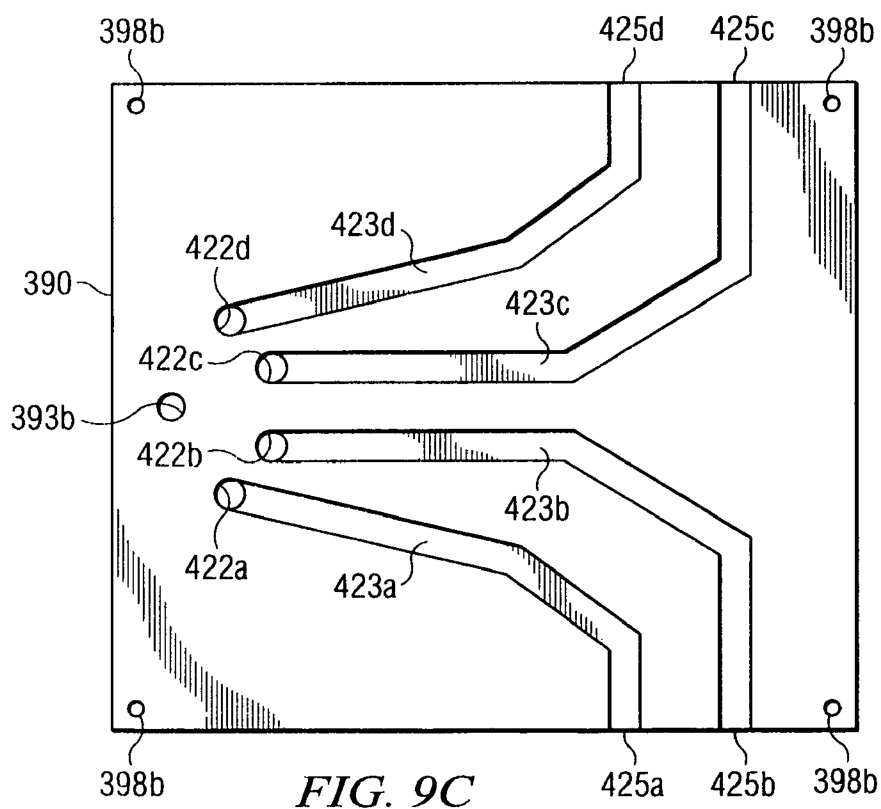

Hot plate 390 is described with the aid of FIGS. 9A and 9B in conjunction with FIG. 2, the upper surface of hot plate 390 being shown in FIG. 9A and cross section being shown in FIG. 9B with relations to other components shown in FIG. 2. A set of cement channel input holes 422*a*, 422*b*, 422*c* and 422*d* are clear holes from the upper surface to the lower surface and adjoin a set of lower cement channels 423*a*, 423*b*, 423*c* and 423*d*, respectively. The lower cement channels are formed by rectangular grooves in the lower surface starting from the cement channel input holes and ending at cement channel output holes 425*a*, 425*b*, 425*c* and 425*d* corresponding to lower cement channels 423*a*, 423*b*, 423*c* and 423*d*, respectively. Hole 393*b* is a clear hole from the upper surface to the lower surface of hot plate 390. Additionally, a set of four holes 398*b* are clear holes from the upper surface to the lower surface near the corners of hot plate 390.

Housing base 304 is a flat plate having hole 393*a* and set of holes 398*a* drilled through from its upper to lower surface. A set of assembly screws 399 are inserted through holes 398*a*, 398*b*, and 398*c* and threaded into threaded hole 398*d* to hold the cement temperature controller 335 together as one piece. Additionally, selector shaft 392 with threads near the upper end is inserted into holes 393*a*, 393*b*, 393*d* in output selector 318 and threaded into threaded hole 393*d* to hold output selector 318 in place so that transit hole 417 may align by rotation of output selector 318 with one of the set of cement channel input holes 422*a*, 422*b*, 422*c* and 422*d* to create an opening from cement receiver 383 to upper cement channel 388 through transit hole 417 and into the lower cement channel associated to the aligned cement channel input hole.

Luer-lock ports 308 are a fastened to the cement channel output holes 425*a*, 425*b*, 425*c* and 425*d* so that output hoses 307 may be suitably attached.

Figure 6A:
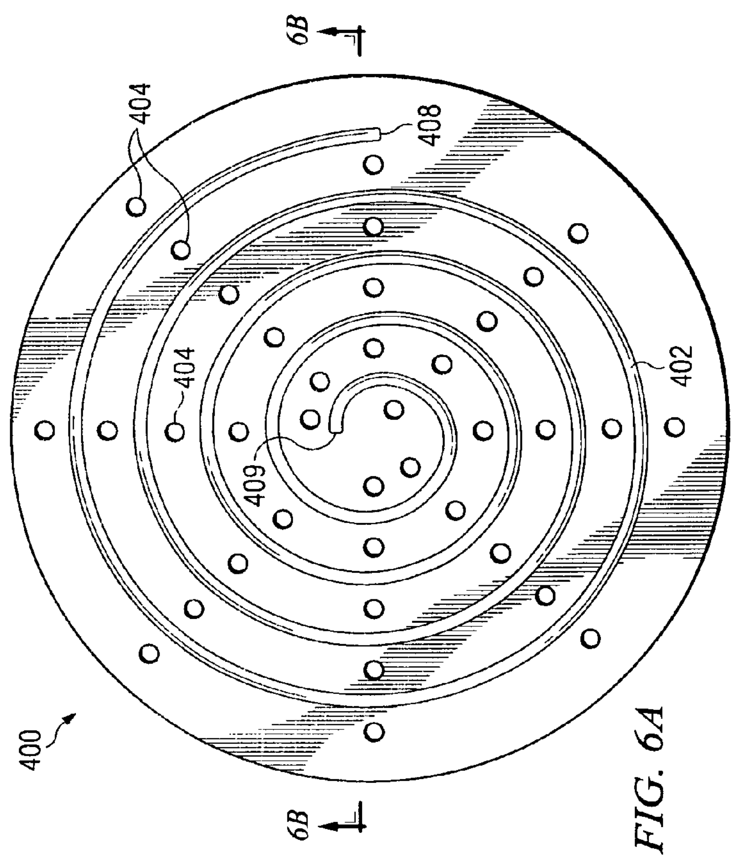
FIGS. 6A and 6B are top and side view drawings of the disposable cement cartridge of the first exemplary embodiment.
Figure 6B:
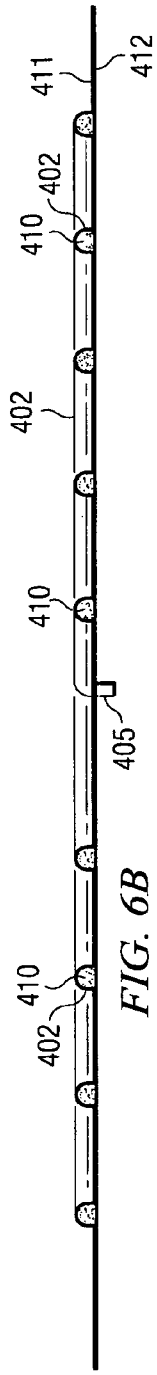

Cement cartridge 400 is shown in detail in FIGS. 6*a* and 6*b* wherein a foil bottom layer 412 is adjoined to a foil upper layer 411 to form cement cartridge 400. A spiral cement pocket 402 forms a bubble on the top surface of cement cartridge 400, spiraling from the outer radius at position 408 to an inner radius at position 409 and into an output nozzle 405 formed on the lower surface of cement cartridge 400. Spiral cement pocket 402 is pressure filled with PMMA cement 410, an exemplary PMMA cement being KyphX® HV-R™ bone cement from Kyphon Corporation. A set of guide holes 404 perforate the foil at various locations outside of the spiral cement pocket 402, the pattern and sizes of the set of guide holes 404 matching the pattern and sizes of the set of standoff pins 382 in cold plate 380.

Figure 10:
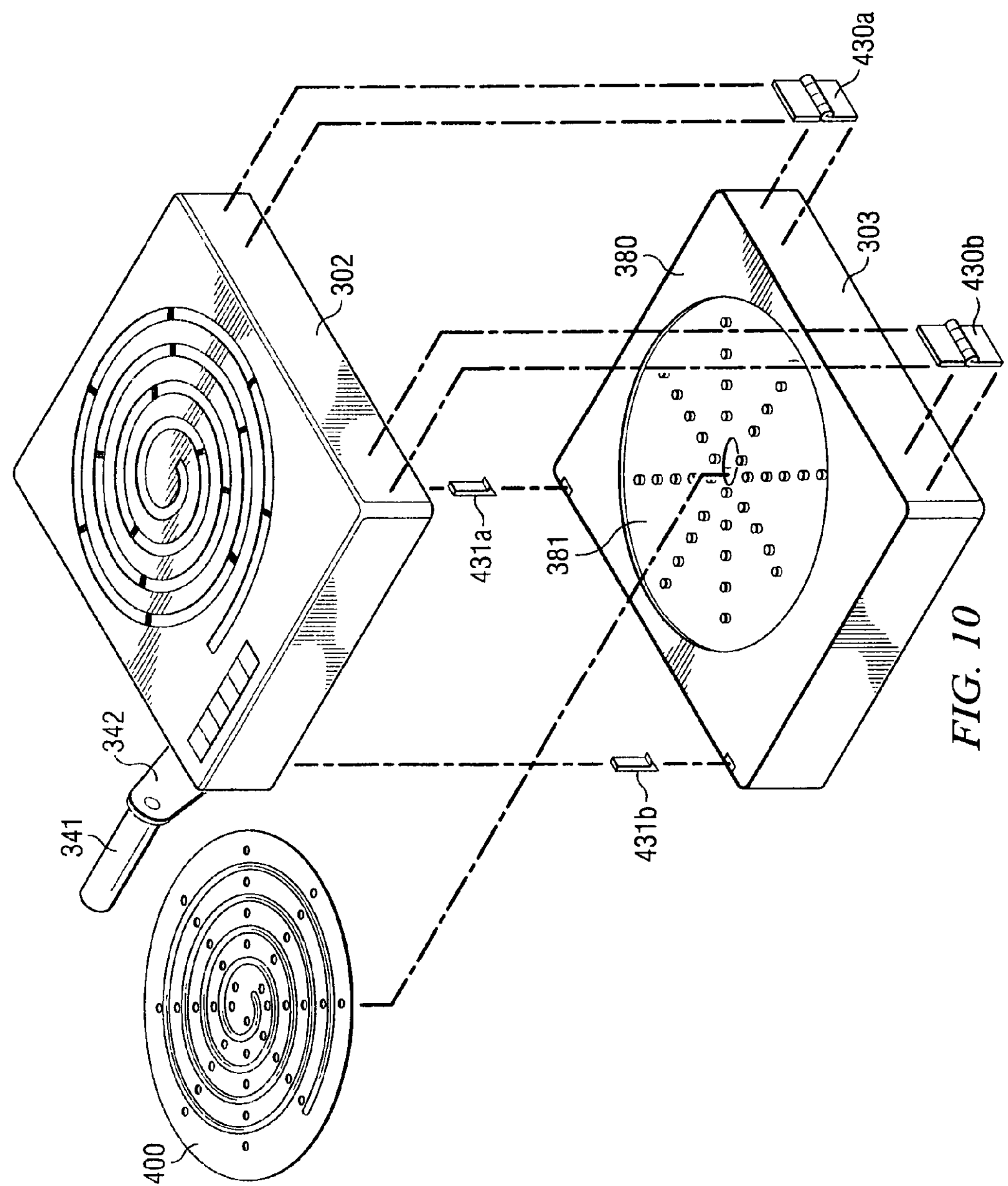
FIG. 10 is a rear view exploded isometric drawing of the first exemplary embodiment of a bone cement dispenser.

Referring to FIG. 10, upper housing cover 302 is securely attached with screws to cement extractor assembly 330 and lower housing cover 303 is securely attached to housing base 304 of temperature controller 335. Upper housing cover 302 is attached to lower housing cover 303 with a set of hinges 430*a* and 430*b* and a set of latches 431*a* and 431*b*, upper housing cover 302 forming a lid which opens to the top surface of cold plate 380.

Figure 11:
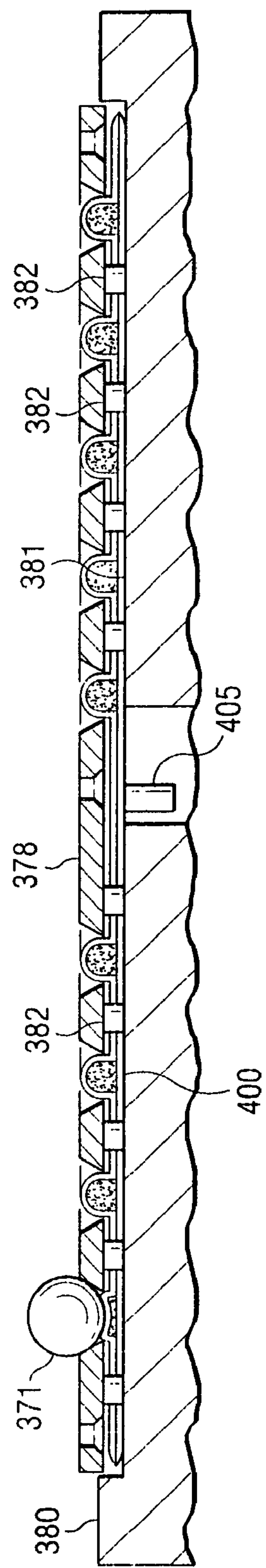
FIG. 11 is a side view drawing of the extractor and cement cartridge interface of the first exemplary embodiment.

In operation, output hoses 307 are attached to Luer-lock ports 308 of cement dispenser 300 with their output ends suitably placed in desired bone locations. Upper housing cover 302 is rotated away from lower housing cover 303 and cement cartridge 400 is positioned over standoff pins 382 atop the surface of cylindrical hollow 381 of cold plate 380. Prior to the positioning of cement cartridge 400 the end of output nozzle 405 is punctured to create a path for cement 410 to exit from spiral cement pocket 402. Once the upper housing cover 302 is closed and latched, cement cartridge 400 is adjacent to and covered by spiral ball guide 378 according to FIG. 11. Extractor ball 371 is pressed into spiral ball guide 378 by extractor disc 370 so that extractor ball 371 is in contact with and depresses spiral cement pocket 402 at the point of contact. Crank 311 is rotated causing extractor disc 370 to rotate via contact with threaded shaft 355. As extractor disc 370 rotates, extractor ball 371 moves along spiral guide 378 depressing spiral cement pocket 402 and ultimately forcing cement 410 through output nozzle 405 and into cement receiver 383.

Peltier junction plate 385 has a voltage, V, applied via electrical cable 316 so that heat is being pumped from cold plate 380 to hot plate 390 subsequently creating a stable temperature difference, ΔT, between the cold and hot plates, wherein ΔT is proportional to V. Cement 410 is cooled since cement cartridge 400 is in contact with cold plate 390. As cement 410 flows from cement receiver 383 into upper cement channel 388, cement 410 remains cooled which retards cement polymerization.

Output selector 318 is rotated to a desired position allowing for the flow of cooled cement 410 into one of the set of lower cement channels and ultimately out of a chosen output port so that cement is dispensed to a desired bone location associated with the output port and output hose. While cement 410 flows through the lower cement channels it is warmed to a temperature ΔT above that of the cooled cement in the cement cartridge. As cement 410 is warmed, its polymerization rate is increased according to the Arrhenius equation so that cement 410 is dispensed to the desired bone location with a desired cement viscosity so that the cement sets up to a desired strength in a desired timeframe. To better enable the desired set up time and viscosity, cement 410 is mixed with potassium permanganate to create a polymerization dependent color, and hence viscosity dependent color. As cement 410 exits through output hoses 307, its color may be matched to a viscosity with the aid of color indicator 315. The correlation between color, temperature and desired characteristics of cement set up may be determined empirically or by other methods known in the art. In another embodiment, a transparent window to the upper cement channel in cold plate 380 may be used to observe cement color in the cooled state.

Once a desired bone location has received enough cement 410, a second desired bone location may be selected by rotating output selector 318 and repeating the given process. Cement dispenser 300 may be cleaned by inserting a cleaning cartridge. The cleaning cartridge is filled with acetone or some other suitable solvent. More aggressive cleaning may be accomplished by removing housing base 304 from the cement temperature controller assembly 335 to access the lower cement channels. Alternatively, some or all of the pieces of the device may be made disposable.

Figure 12A:
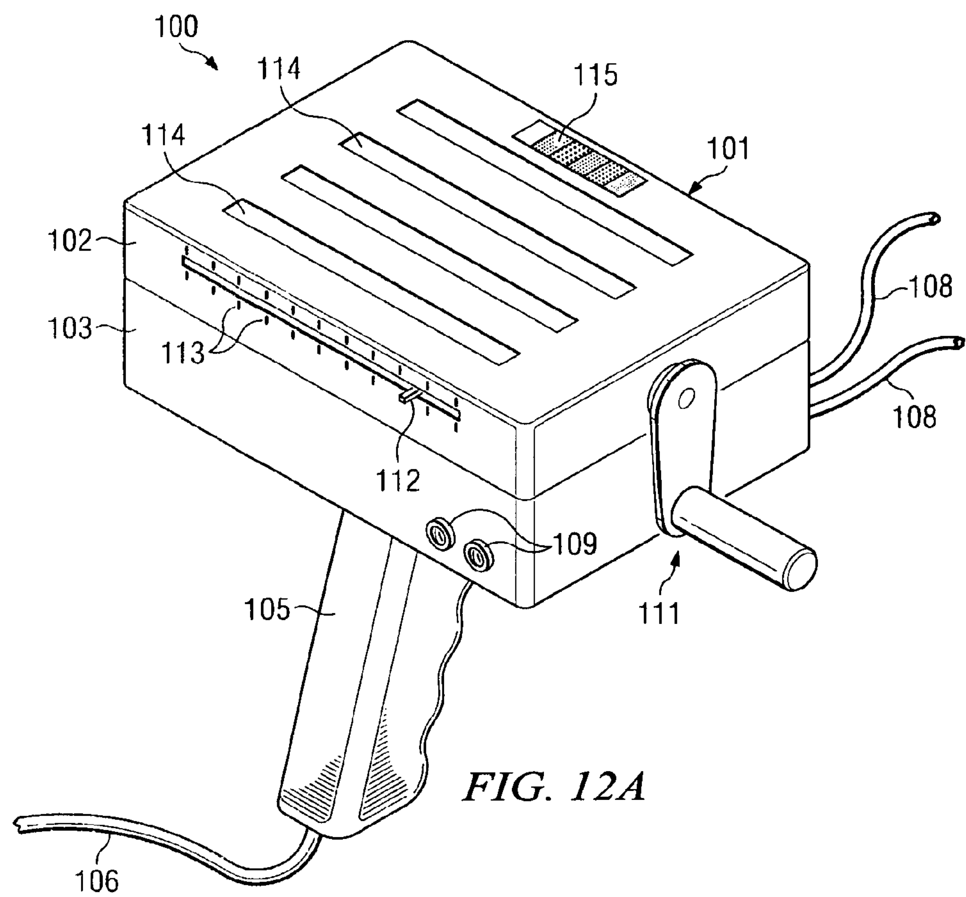
FIG. 12A is a front view isometric drawing of a second exemplary embodiment of a handheld bone cement dispenser.

Referring now to FIG. 12A, a second exemplary embodiment of a bone cement dispenser 100 commensurate with the present invention is shown in perspective drawing. Bone cement dispenser 100 has housing 101 comprised of upper housing cover 102, a lower housing plate 103 and handle 105 attached to lower housing plate 103 so that bone cement dispenser 100 may be held firmly by hand while in operation. Furthermore, a set of four Luer-lock ports 109 are fixed to housing 101 to which a set of outlet hoses 108 are attached, outlet hoses 108 providing a path for cement to flow from bone cement dispenser 100 to the point of operation, for example, a human vertebra. The set of outlet hoses 108 are made of clear plastic. Bone cement is stored in a disposable cement cartridge held firmly inside dispenser 100, the disposable cement cartridge being described further below in relation to FIGS. 21A, 21B and 21C.

Figure 14:
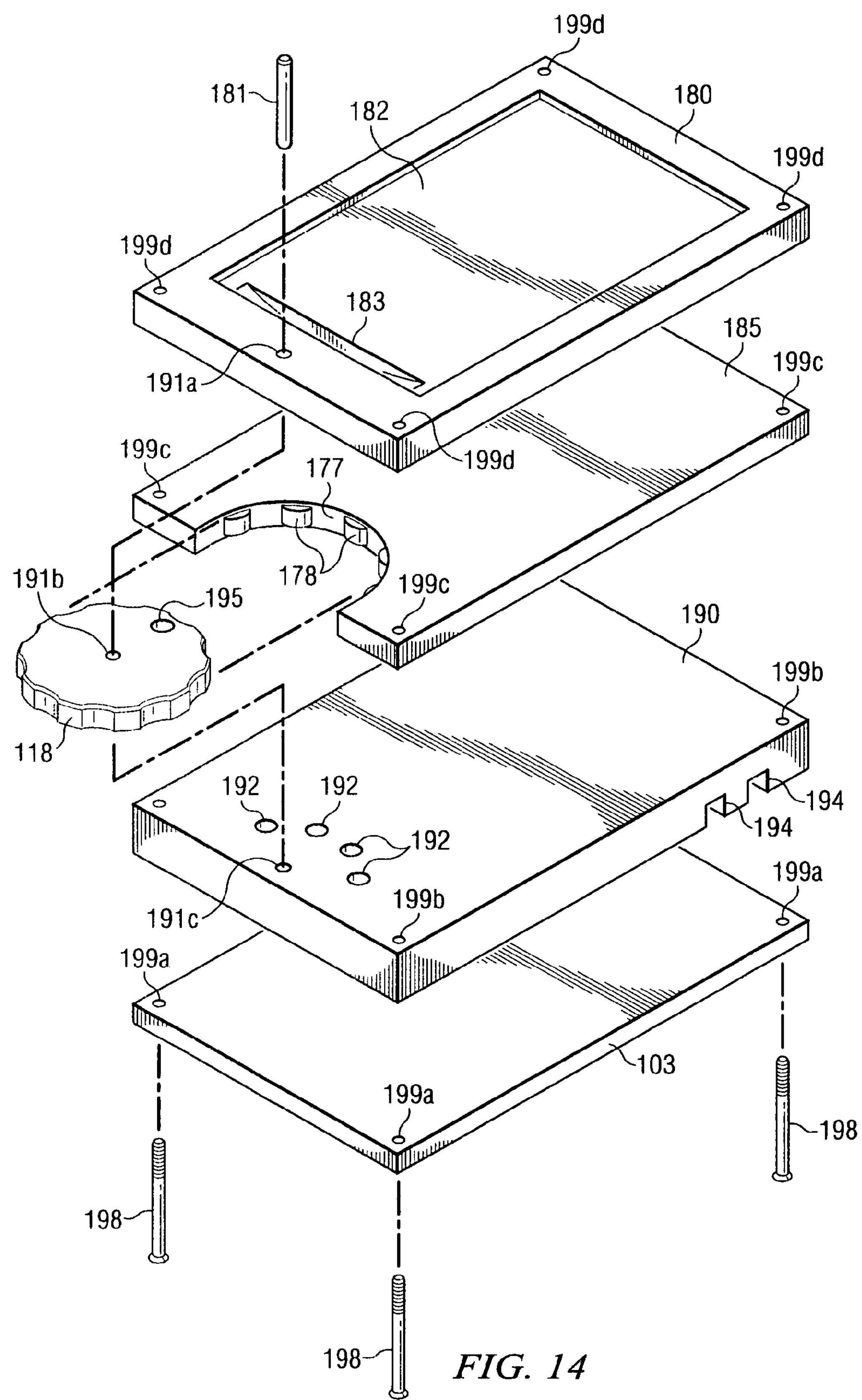
FIG. 14 is an exploded isometric drawing of the cement dispensing mechanism of the second exemplary embodiment.

Crank 111 is rotatably attached through housing 101 to a cement dispensing mechanism contained therein for causing cement to be dispensed from the disposable cement cartridge into the set of outlet hoses 108. An indicator 112 protruding through one side of housing 101 is provided in combination with a set of calibrated graticules 113 marked on the same side of housing 101, the combination being useful for indicating a quantity of cement dispensed. Color chart 115 is placed on the outside of housing 101 for indicating cement viscosity. Furthermore, a set of clear windows 114 allow for viewing of cement as it is dispensed. A temperature controller device, explained in connection with FIG. 14, is contained in housing 101 and powered through electrical cable 106. Viscosity of cement is controlled by cooling stored cement in the disposable cement cartridge and then heating dispensed cement as it moves from the cartridge to the Luer-lock ports 109.

Figure 12B:
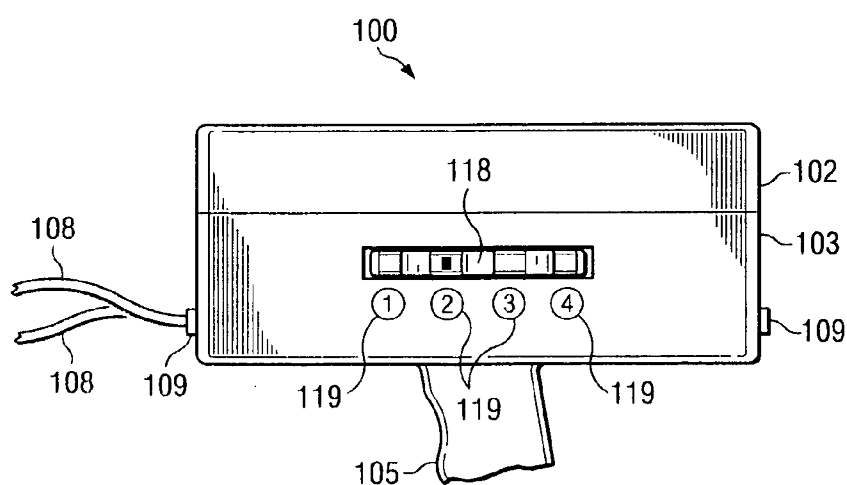
FIG. 12B is a rear view of the second exemplary embodiment of a handheld bone cement dispenser.

FIG. 12B shows a rear perspective view of bone cement dispenser 100. Outlet selector 118 is a rotatable selector wheel which selects between positions 119, each position correspondingly allowing cement to dispense through one of the four respective Luer-lock outlet ports 109.

Figure 13A:
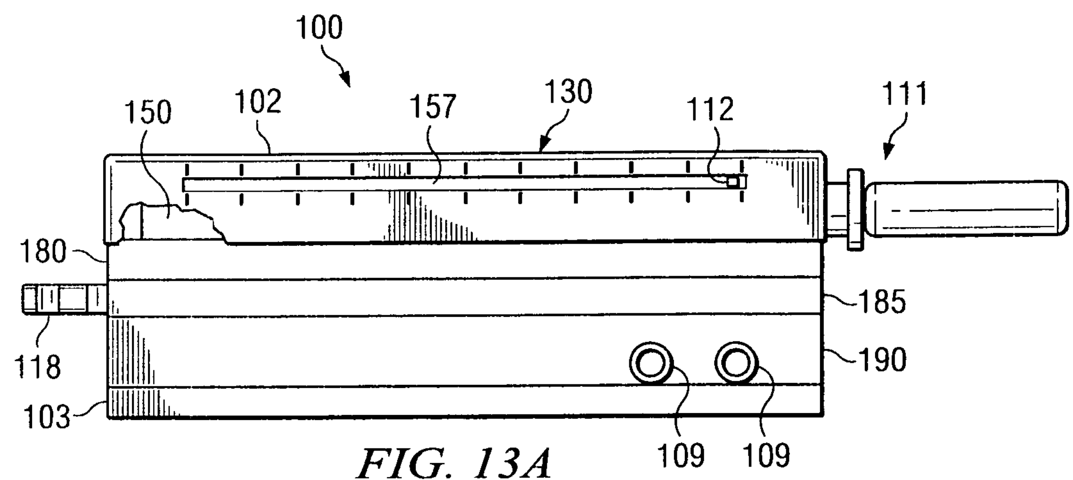
FIGS. 13A, 13B and 13C are side, top and bottom views, respectively, of the cement dispensing mechanism of the second exemplary embodiment.
Figure 13B:
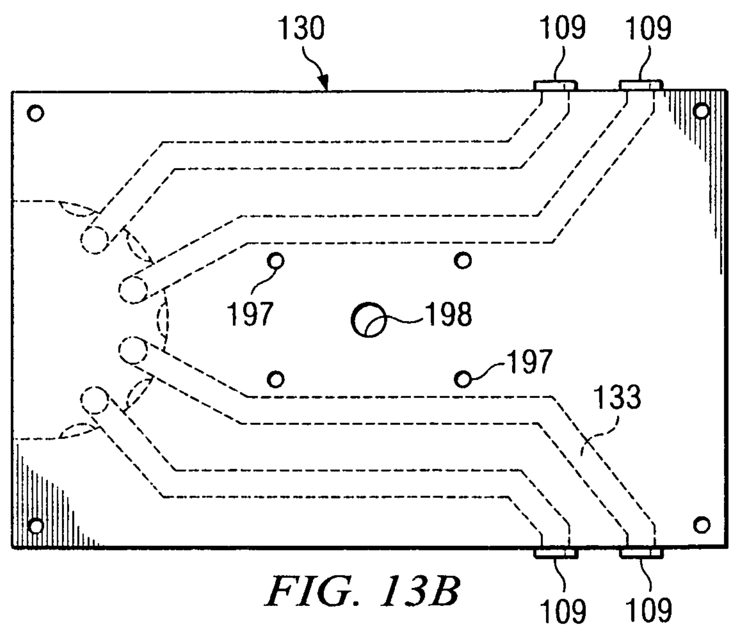
Figure 13C:
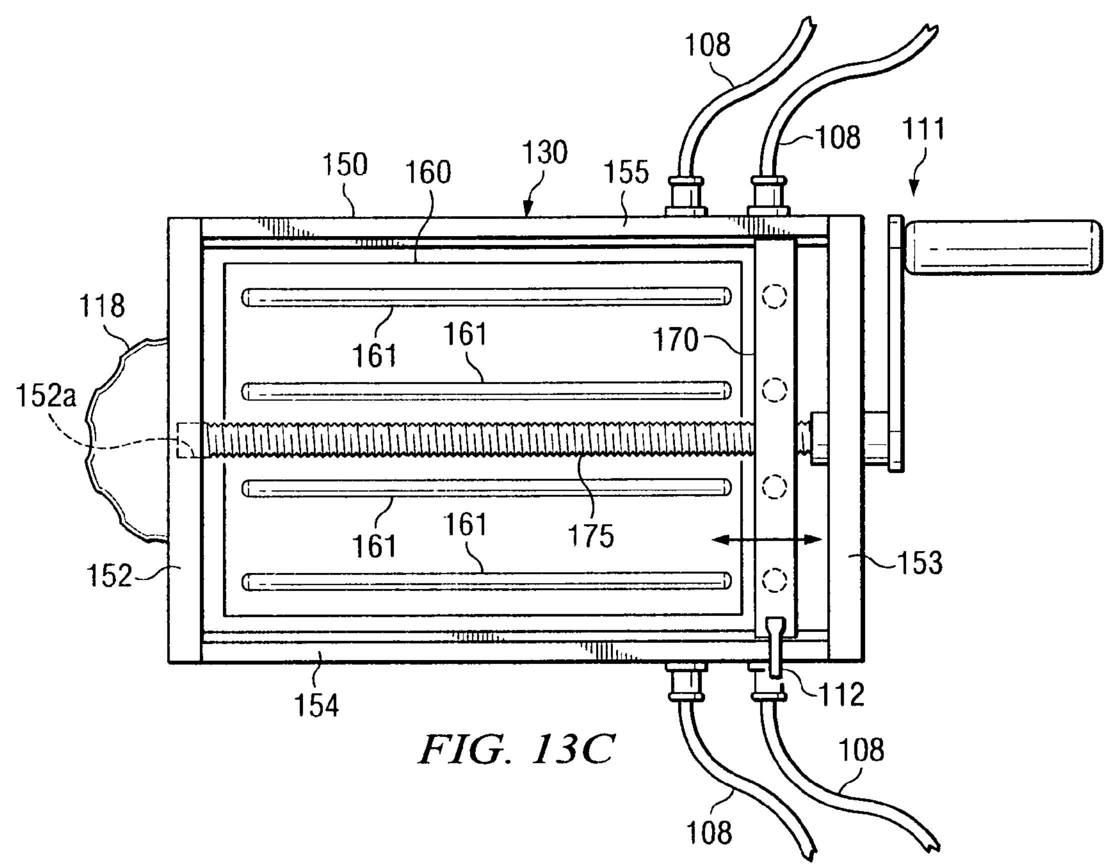

Detailed views of the cement dispensing mechanism contained within bone cement dispenser 100 are shown in FIGS. 13A, 13B and 13C. FIG. 13A shows a side view of cement dispensing mechanism 130 which is attached to lower housing plate 103, upper housing cover 102 normally covering cement dispensing mechanism 130. Cement dispensing mechanism 130 comprises cement extractor 150 adjacent to the top of cold plate 180, cement extractor 150 having crank 111 attached thereto and having an indicator slot 157 for indicator 112. Peltier junction block 185 separates cold plate 180 in a first temperature controlled region from hot plate 190 in a second temperature controlled region. Cold plate 180 and hot plate 190 are affixed to Peltier junction block 185, cold plate 180 being affixed to the cold side of Peltier junction block 185 and hot plate 190 being affixed to the hot side of Peltier junction block 185. Output selector 118 is positioned between cold plate 180 and hot plate 190. Luer-lock ports 109 are fastened to lower housing plate 103 and are connected to cement channels 133 inside hot plate 190.

Lower housing plate 103 is attached to the bottom side of hot plate 190. The drawing of FIG. 13B shows that lower housing plate 103 contains mounting holes 197 and a hole 198 for placing electrical wires to power the Peltier cooling block. When a DC voltage V is applied to Peltier cooling block 185, heat is transferred from cold plate 180 to hot plate 190, causing cold plate 180 to attain a temperature lower than ambient temperature and hot plate 190 to attain a temperature higher than ambient temperature, the temperature difference ΔT between cold plate 180 and hot plate 190 being proportional to V.

The heating and cooling elements comprising cement dispensing mechanism 130 are further explained with the aid of FIGS. 14 through 16. Beginning with FIG. 14, Peltier plate 185 is sandwiched between cold plate 180 and hot plate 190, the assembly being fastened together by screws 198 inserted through lower housing plate 103 through sets of holes 199*a*, 199*b* and 199*c* into threaded holes 199*d* machined into cold plate 180. A thermally conductive paste may be applied to the top and bottom surfaces of Peltier plate 185 to effect an efficient thermal path to the cold and hot plates, respectively. Output selector 118 having a central hole 191*b* and a cement transit hole 195 is inserted into selector slot 177 which is a semicircular cutout in Peltier plate 185. Pin 181 is placed through hole 191*a* of cold plate 180, through the central hole 191*b* of output selector 118 and into hole 191*c* of hot plate 190 so that output selector 118 may rotate to preferably align cement output hole 195 with a given cement channel hole of the set of cement channel holes 192 in hot plate 190. A set of index bumps 178 are machined into selector slot 177 to aid in positioning output selector 118 to effect alignment of the given cement channel hole to the cement transit hole 195.

Cold plate 180 has a cartridge receiver area 182 for holding disposable cement cartridges containing PMMA cement. PMMA cement is received through cement receiver 183 which is a slot through which PMMA cement may flow from the top surface of cold plate 180 through cement transit hole 195 to one of the set of cement channel holes 192 aligned thereto. Cement channels (not shown) in hot plate 190 allow cement to flow through hot plate 190 to cement output ports 194.

Figure 15A:
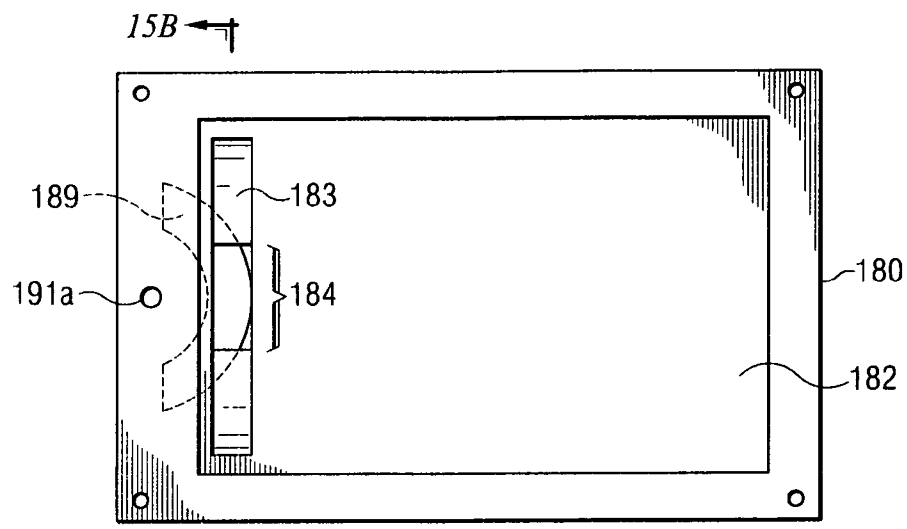
FIGS. 15A, 15B and 15C are top, cross-section and bottom views, respectively, of the cold plate of the second exemplary embodiment.
Figure 15B:
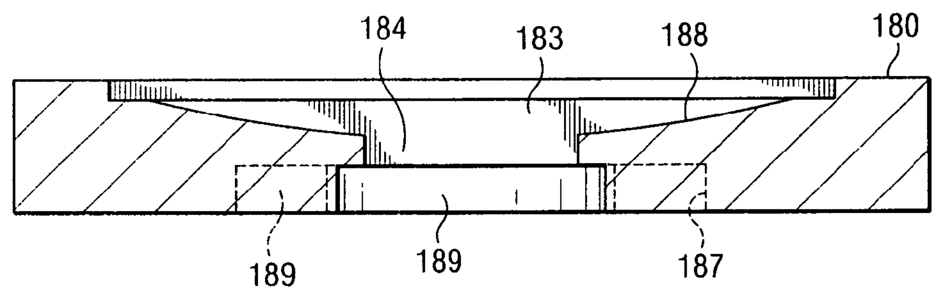
Figure 15C:
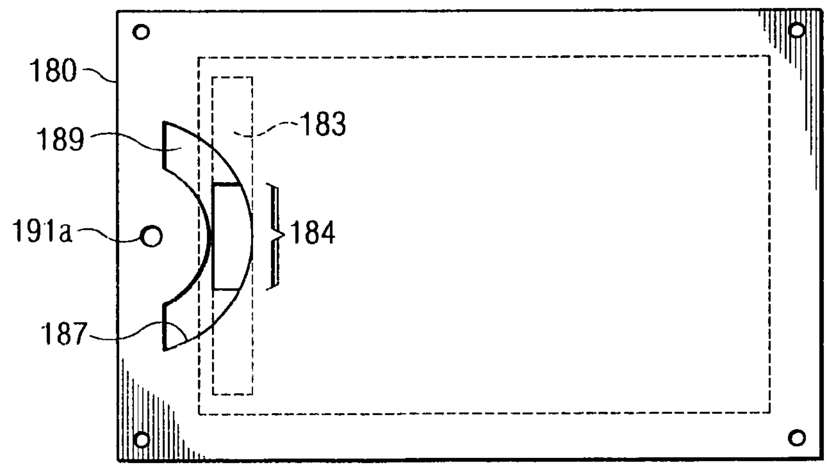

Detail of cold plate 180 is shown in FIGS. 15A, 15B and 15C. Cartridge receiver area 182 is a rectangular pan structure of approximately 3 mm depth into which a disposable cement cartridge is placed. Cement receiver slot 183 is machined into the top surface of cold plate 180 at one end having at least the width of the disposable cement cartridge. Hole 191*a* is a clear hole for holding pin 181. A cross sectional view of cold plate 180 in FIG. 15B shows that cement receiver 183 has a curved wall 188 in connection with through-slot 184. A semicircular cement distribution slot 189 is cut into the bottom surface of cold plate 180, the wall 187 of distribution slot 189 being in contact with through-slot 184.

Figure 16A:
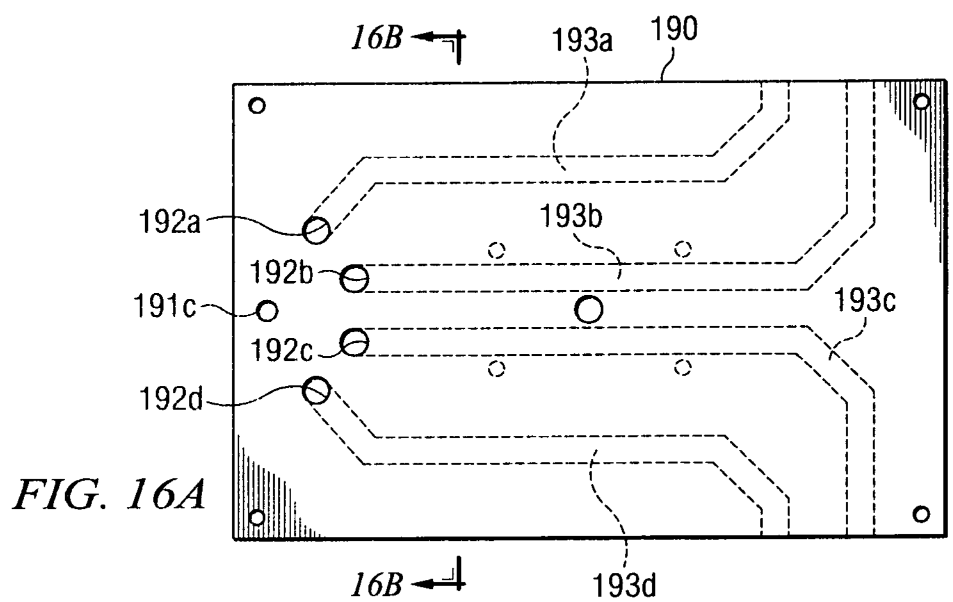
FIGS. 16A, 16B and 16C are top, cross-section and bottom views, respectively, of the hot plate of the second exemplary embodiment.
Figure 16B:
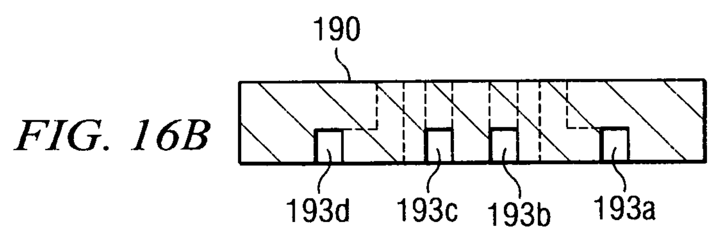
Figure 16C:
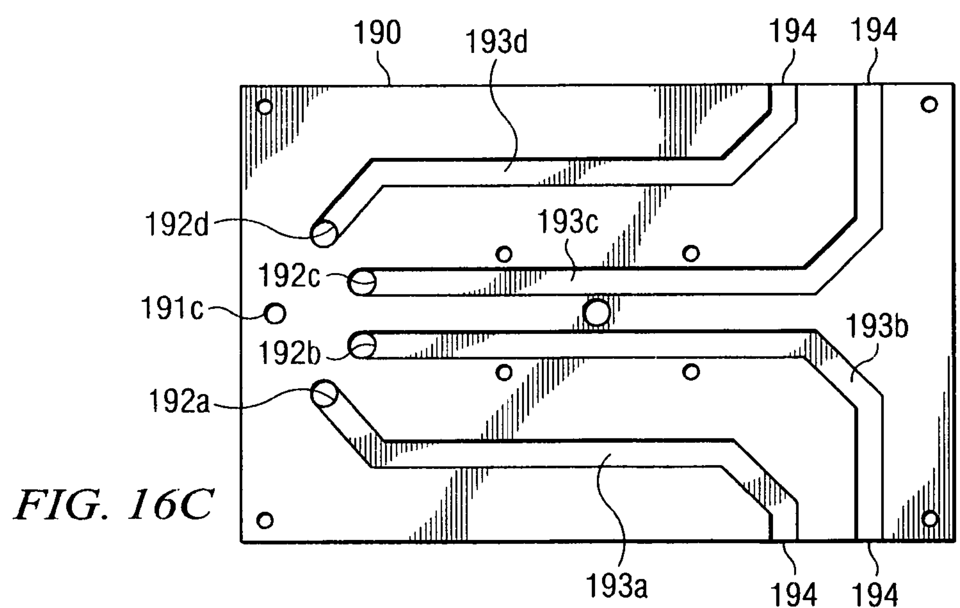

Detail of hot plate 190 is shown in FIGS. 16A, 16B and 16C. The top surface of hot plate 190 has four holes 192*a*, 192*b*, 192*c* and 192*d* drilled through to cement channels 193*a*, 193*b*, 193*c* and 193*d*, respectively. Cement channels 193*a*, 193*b*, 193*c* and 193*d* are rectangular channels cut approximately 3 mm deep into the bottom surface of hot plate 190, running along the length of hot plate 190 and connecting to the outside through cement output ports 194 which have Luer-lock connectors 109 attached thereto.

Returning now to FIG. 13C, a drawing showing the top view of cement extractor 150 is shown with upper housing cover 102 removed. Cement extractor 150 has right rail 155 and left rail 154, both rails attached to end plate 152 and further attached to end plate 153, the rails and end plates forming a fixed frame. Rails 154 and 155 are machined to accept a moveable extractor press 170 which slides along rails 154 and 155, the extractor press having indicator 112 attached thereto. Crank 111 is attached to a threaded shaft 175 which is held in a freely rotatable position between end plate 152 and end plate 153. Threaded shaft 175 is threaded through a hole in extractor press 170 so that upon rotating crank 111, threaded shaft 175 causes extractor press 170 to linearly move in a direction parallel to rails 154 and 155. Underneath extractor press 170 is a disposable cement cartridge 160 having a set of cement packets 161 running the length of disposable cement cartridge 160 in a direction parallel to rails 154 and 155 and protruding upward, disposable cement cartridge 160 being placed in cartridge receiving area 182 of cold plate 180.

Figure 17A:
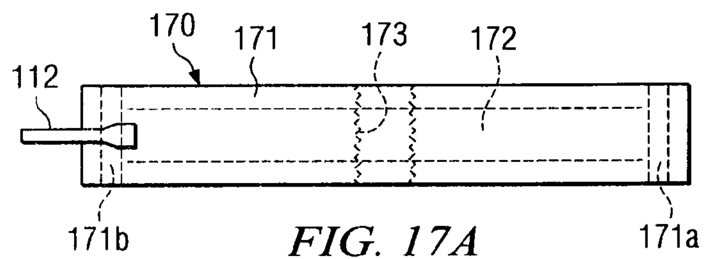
FIGS. 17A, 17B and 17C are top, side and end views, respectively, of the extractor press of the second exemplary embodiment.
Figure 17B:
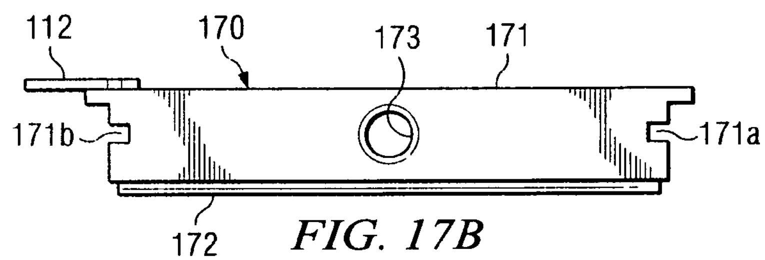
Figure 17C:
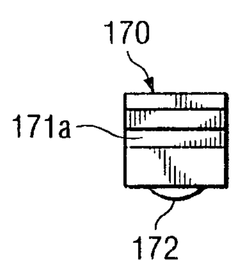

FIGS. 17A, 17B and 17C show more detail of extractor press 170 in a top, side and end view, respectively. Extractor press 170 has indicator 112 attached to its top surface 171. Extractor press 170 also has a pair of slots 171*a* and 171*b* on either side into which rails 154 and 155 are inserted. A cylindrical protrusion 172 extends to form a bottom surface. Hole 173 is threaded through extractor press 170 through which threaded shaft 175 is run.

Figure 17D:
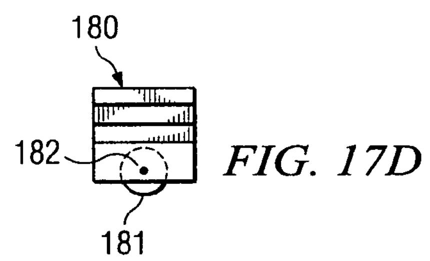
FIG. 17D is an end view of an alternative embodiment of an extractor press.

FIG. 17D shows an end view of another exemplary embodiment of extractor press 170 wherein a cylindrical roller 181 rotates on axis 182.

Figure 18:
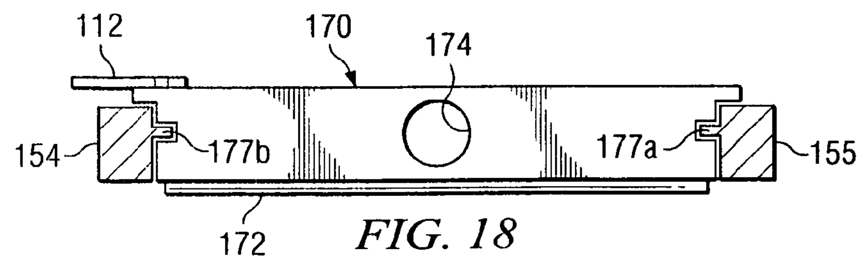
FIG. 18 is an end view of the cement extractor of the second exemplary embodiment.

FIG. 18 shows cement extractor 150 frame as viewed towards end plate 153. End plate 153 has clear hole 174 for mounting threaded shaft 175. Left rail 154 has lip 177*a* and right rail 155 has lip 177*b* which are inserted into slots 171*a* and 171*b*, respectively. Indicator 112 protrudes from the side of cement extractor 150 nearest left rail 155.

Figure 19:
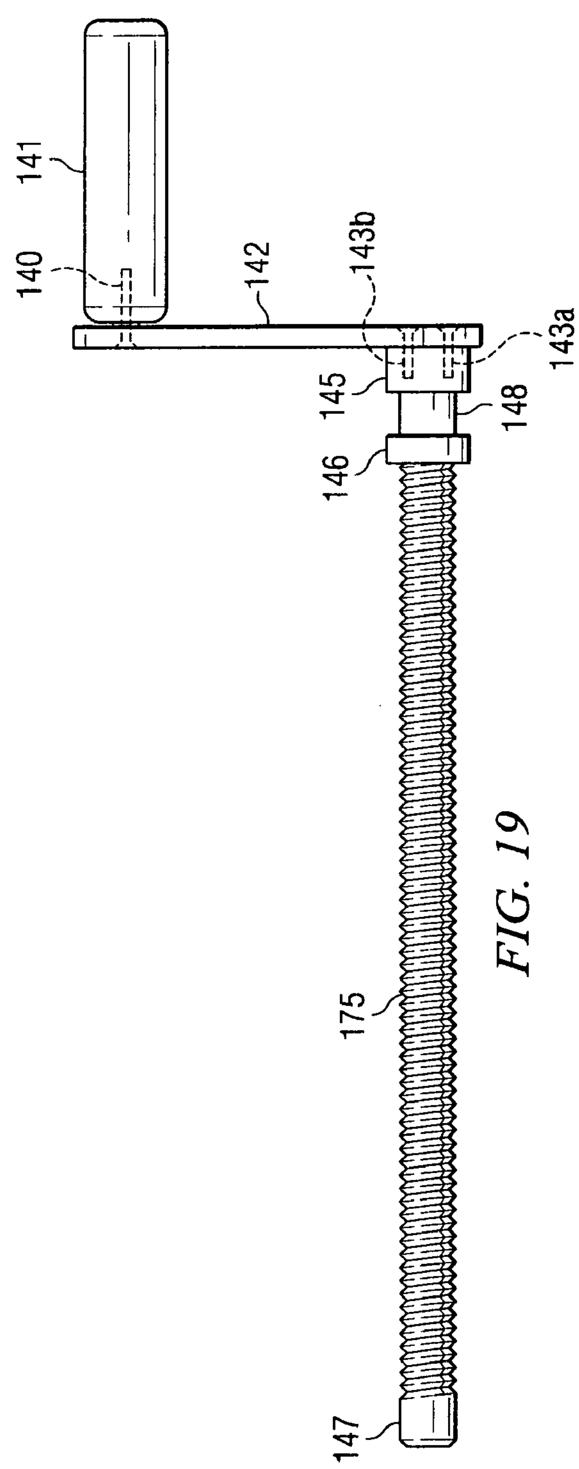
FIG. 19 is a side view of the crank mechanism of the second exemplary embodiment.

In FIG. 19, a drawing of crank 111 is shown, crank 111 comprising threaded shaft 175 to which arm 142 is attached with screws 143*a* and 143*b* and a handle 141 attached to arm 142 with rivet 140. Collar 146 is fastened to collar end shaft 148 near shoulder 145, collar end shaft 148 being inserted into clear hole 174 of end plate 153 with collar 146 fastened just inside end plate 153 and shoulder 145 placed just outside end plate 153 to hold threaded shaft 175 rotatably in the fixed frame of cement extractor 150. Smooth end shaft 147 is placed into hole 152*a* (shown in FIG. 13*c*) drilled into end plate 152 and opposite clear hole 174.

Alternative embodiments are conceived wherein other rotational means may cause rotation of threaded shaft 175. Handle 141 and arm 142 may be replaced with other suitable coupling means between threaded shaft 175 and the rotational means. For example, a stepper motor may be coupled to threaded shaft 175 to effect rotation. Also, simple improvements may be conceived wherein rotational bearings may be inserted into end plate 153 for holding shoulder 145 and inserted into end plate 152 for holding shaft 147. Linear bearing devices may be used in place of the lip and slot rail system to increase durability and accuracy of the extractor press movement.

Figure 23:
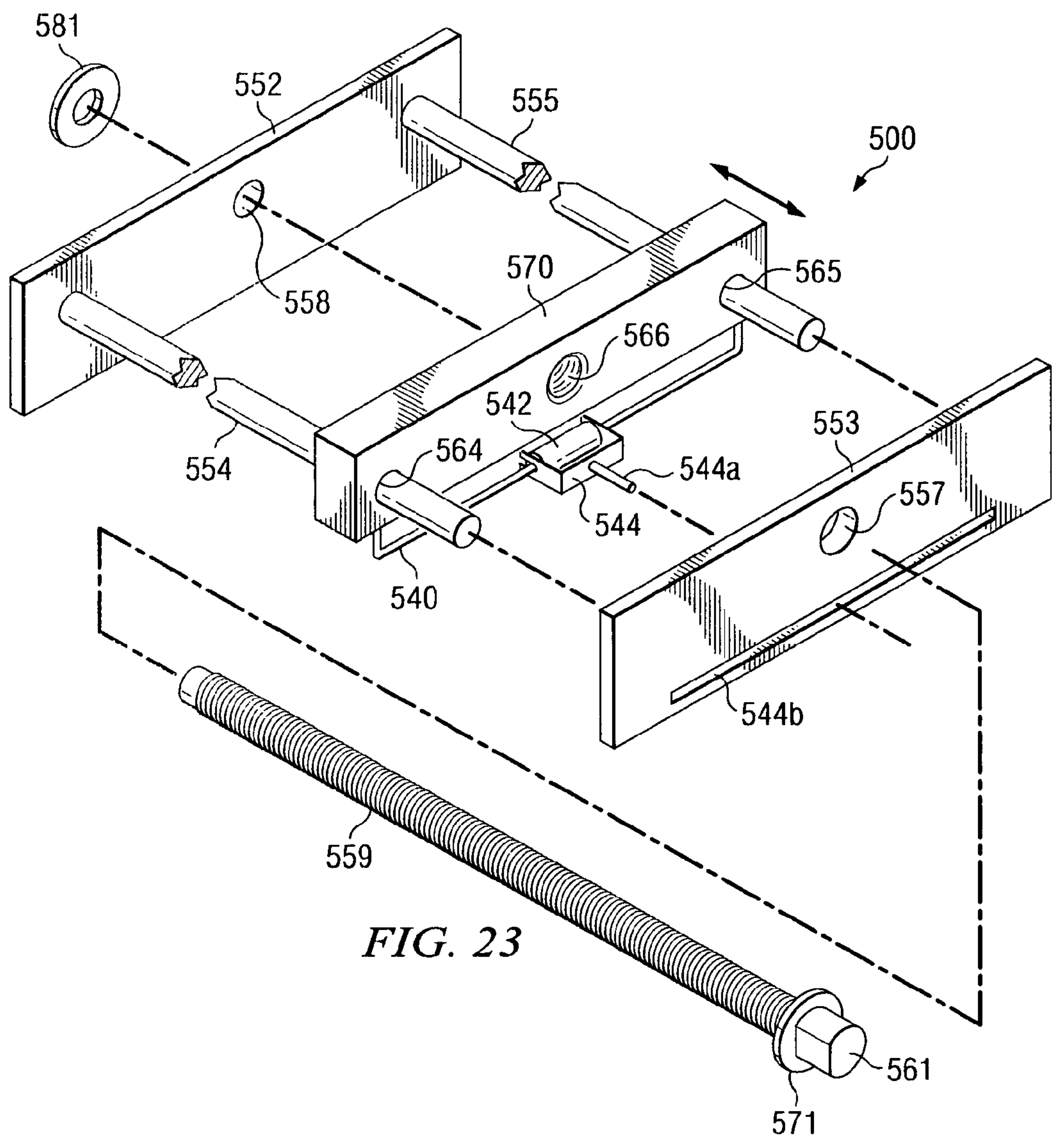
FIG. 23 is a perspective drawing of a bone cement extractor of an alternate embodiment of the present invention.

FIG. 23 is a perspective drawing of an alternate cement extractor 500 which is comprised of guide bars 554 and 555 each fastened to end plate 552 and to end plate 553 to form a rigid structure. Extractor press 570 has guide holes 564 and 565 into which guide bars 554 and 555 are inserted so that extractor press 570 can be moved linearly along the guide bars. Holes 557 and 558 in the end plates allow the placement of threaded shaft 559 through threaded hole 566 to effect linear movement of extractor press 570. A spanner connection 561 is provided for attachment of a handle or motor drive (not shown). Retaining collars 571 and 581 retain the threaded rod in end plates 552 and 553 respectively. A roller rod 540 having dispensing roller 542 placed thereon, is fastened to the lower side of extractor press 570. Dispensing roller 542 may slide laterally along roller rod 540. Reservoir selector 544 surrounds dispensing roller 542 and is guided by roller rod 540, and may be used to preferably position dispensing roller 542 over a cement packet to extract cement therefrom. A pin 544*a* extends through slot 544*b* in end plate 553 to align reservoir selector 544.

Figure 24:
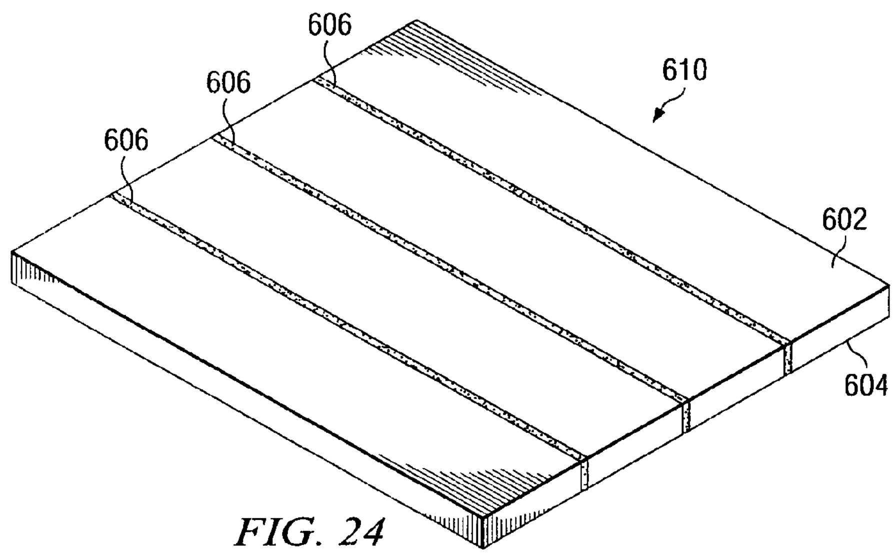
FIG. 24 is a perspective drawing of an array of independently controlled Peltier junction devices of an alternate embodiment of the present invention.
Figure 25:
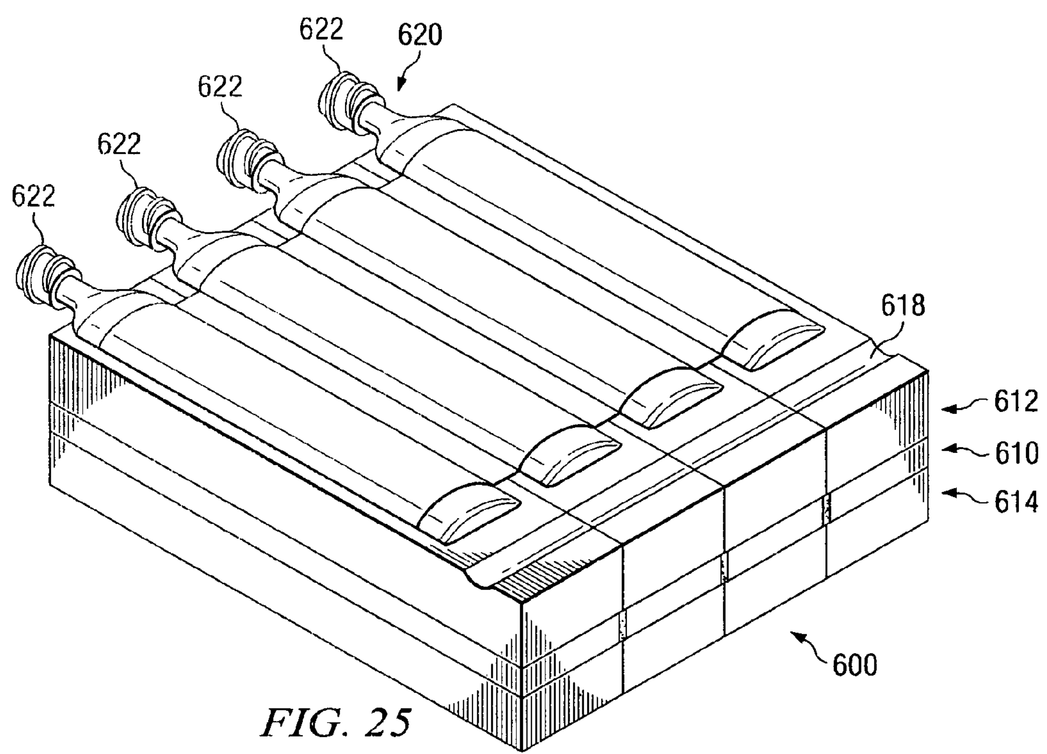
FIG. 25 is a perspective drawing of a cement temperature controller of an alternate embodiment of the present invention.

FIG. 24 is a perspective drawing of another embodiment of the present invention, showing an array of independently controllable Peltier junction devices 610, each member of the array having cold side 602, hot side 604 and having independent power connections. Each member device of array 610 is thermally insulated from the adjacent member devices of the array by insulating material 606. FIG. 25 shows array 610 in cement temperature controller 600 which is comprised of an array of cold plates 612 and an array of hot plates 614, between which is placed array 610 of Peltier junction devices, cold side 602 of each Peltier junction device being in thermal contact with one of cold plates 612 and hot side 604 being in contact with one of hot plates 614. A set of metallized PMMA cement packets 620 are placed on top of the array of cold plates 612, the set of cement packets 620 having a corresponding set of Luer-lock ports 622 for dispensing the cement into connectable hoses. A depression 618 is fashioned in the top of the cold plates 612 in which the dispensing roller 542 of cement extractor 500 is translated. Cement temperature controller 600 is fixed between end plates 552 and 553 of cement extractor 500 to form an alternate embodiment cement dispenser.

Figure 20:
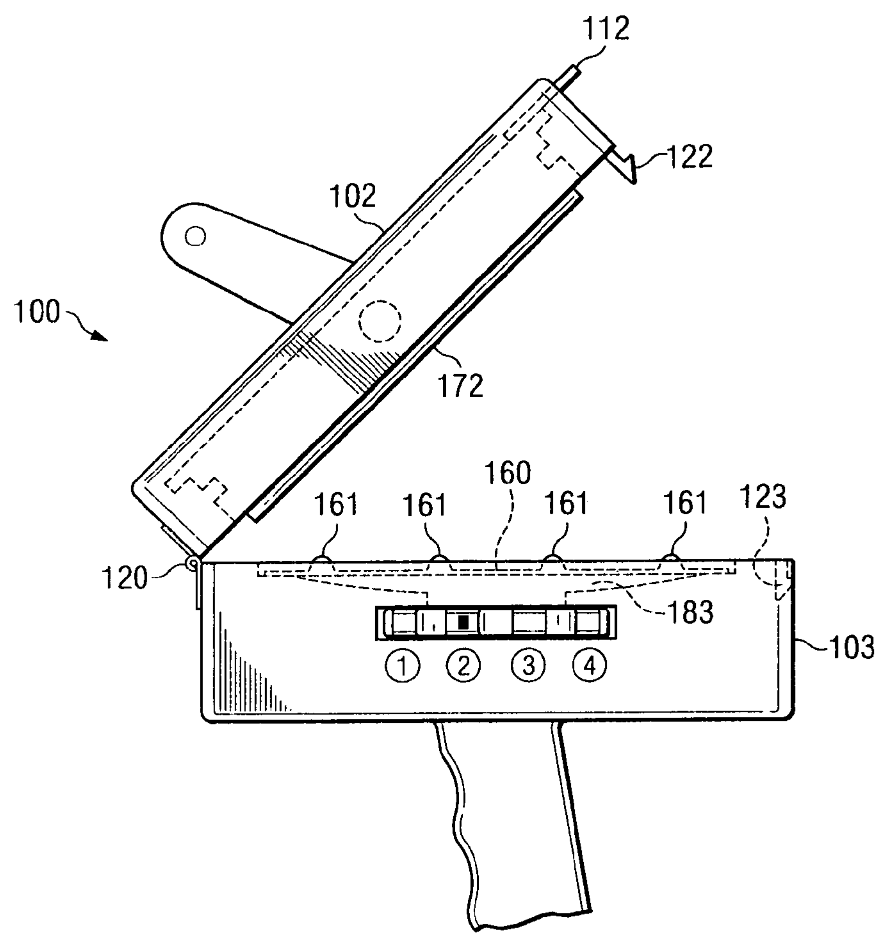
FIG. 20 is an end view of the bone cement dispenser of the second exemplary embodiment.

FIG. 20 shows a side view of bone cement dispenser 100 of FIG. 12B, illustrating the mechanism by which disposable cement cartridges 160 are inserted and removed from bone cement dispenser 100. Upper housing cover 102 is rotationally attached to lower housing plate 103 by hinge 120 so that cement receiving area 183 may be accessed. A set of latches 122 are made to fit into a set of latch receivers 123 to hold upper housing cover 102 firmly to the lower housing plate 103. Once closed, cylindrical protrusion 172 on extractor press 170 applies pressure to cement packets 161.

Figure 21A:
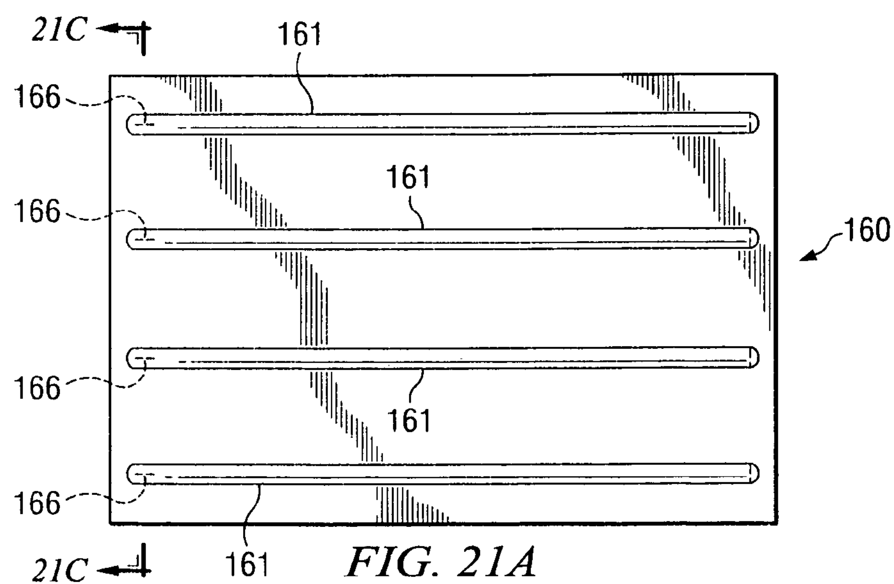
FIGS. 21A, 21B and 21C are top and side views of the disposable cement cartridge of the second exemplary embodiment.
Figures 21B, 21C:
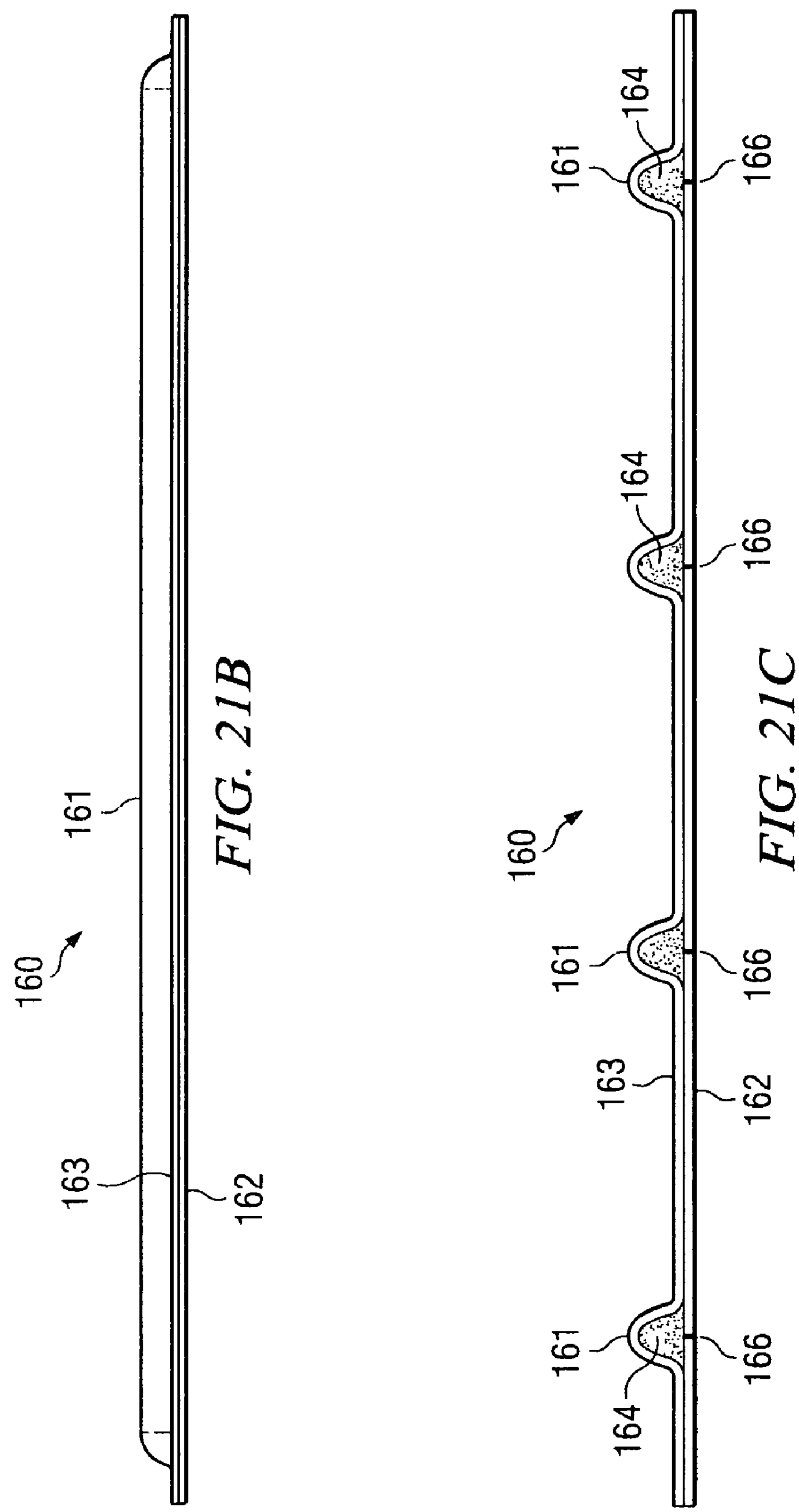

Disposable cement cartridges are a novel and useful means for inertly holding PMMA until ready for dispensing. FIGS. 21A, 21B and 21C show three perspective views of a second exemplary embodiment disposable cement cartridge 160. A foil bottom layer 162 is sealed to foil top layer 163 forming cement packets 161 which are filled with PMMA cement 164 and run the length of cement cartridge 160. At one end of cement cartridge 160 a set of small outlet slits 166 are cut into foil bottom layer 162 during manufacturing. Foil bottom layer 162 is in contact with cold plate 180 when the device is in operation. In an alternate embodiment, foil top layer 163 may be integrated with a transparent material such as plastic to allow for visual inspection of cement 164 while still inside cement packets 161.

Refer to FIGS. 12A through 15 and FIG. 20 for an explanation of the operation of the cement dispenser 100. In operation, output hoses 108 are attached to Luer-lock ports 109 of cement dispenser 100 with their output ends suitably placed in desired bone locations. To begin the operation, PMMA monomer is mixed with PMMA powder to form PMMA cement 164 which is caused to flow into disposable cement cartridge 160 and out of outlet slits 166 just enough to expunge any trapped air in the cartridge. Upper housing cover 102 is rotated away from lower housing base 103 and disposable cement cartridge 160 is positioned on the upper surface of cartridge receiver 182 of cold plate 180. Once the upper housing cover 102 is closed and latched, disposable cement cartridge 160 is adjacent to and covered by cement extractor 150 while cylindrical protrusion 172 is in contact with and depresses cement packet 161 at the point of contact. Crank 111 is rotated causing extractor press 170 to move linearly towards end plate 152, wherein extractor press 170 compresses cement packets 161 causing cement to flow towards end plate 152, out of cement cartridge 160 and into cement receiver 183 of cold plate 180.

Peltier junction plate 185 then has a voltage V applied via electrical cable 106 so that heat is pumped from cold plate 180 to hot plate 190 subsequently creating a stable temperature difference $\Delta T$ between the cold and hot plates, wherein $\Delta T$ is proportional to V. Cement 410 is typically cooled since cement cartridge 160 is in contact with cold plate 190. As cement 164 flows from cement receiver 182 into distribution slot 189, cement 164 is further cooled which decreases the cement temperature discouraging cement polymerization.

Output selector 118 is rotated to a desired position allowing for the flow of cooled cement 164 into one of the set of lower cement channels and ultimately out of a chosen output port so that cement is dispensed to a desired bone location associated to the output port and output hose. While cement 164 flows through the lower cement channels it is warmed to a temperature $\Delta T$ above that of the cooled cement in the cement cartridge. As cement 164 is warmed, its polymerization rate is increased according to the Arrhenius equation so that cement 164 is dispensed to the desired bone location with a desired cement viscosity so that the cement sets up to a desired strength in a desired timeframe similar to the first exemplary embodiment. As cement 164 exits through output hoses 108, its color may be matched to a temperature with the aid of color indicator 115. Clear window 114 may be used to observe the color of PMMA cement prior to being dispensed, wherein cement packets 161 are transparent on the top surface.

Once a desired bone location has received enough cement 164, a second desired bone location may be selected by rotating output selector 118 and repeating the given process. Cement dispenser 100 may be cleaned by inserting a cleaning cartridge. More aggressive cleaning may be accomplished by removing housing base 104 from hot plate 190.

Figure 22:
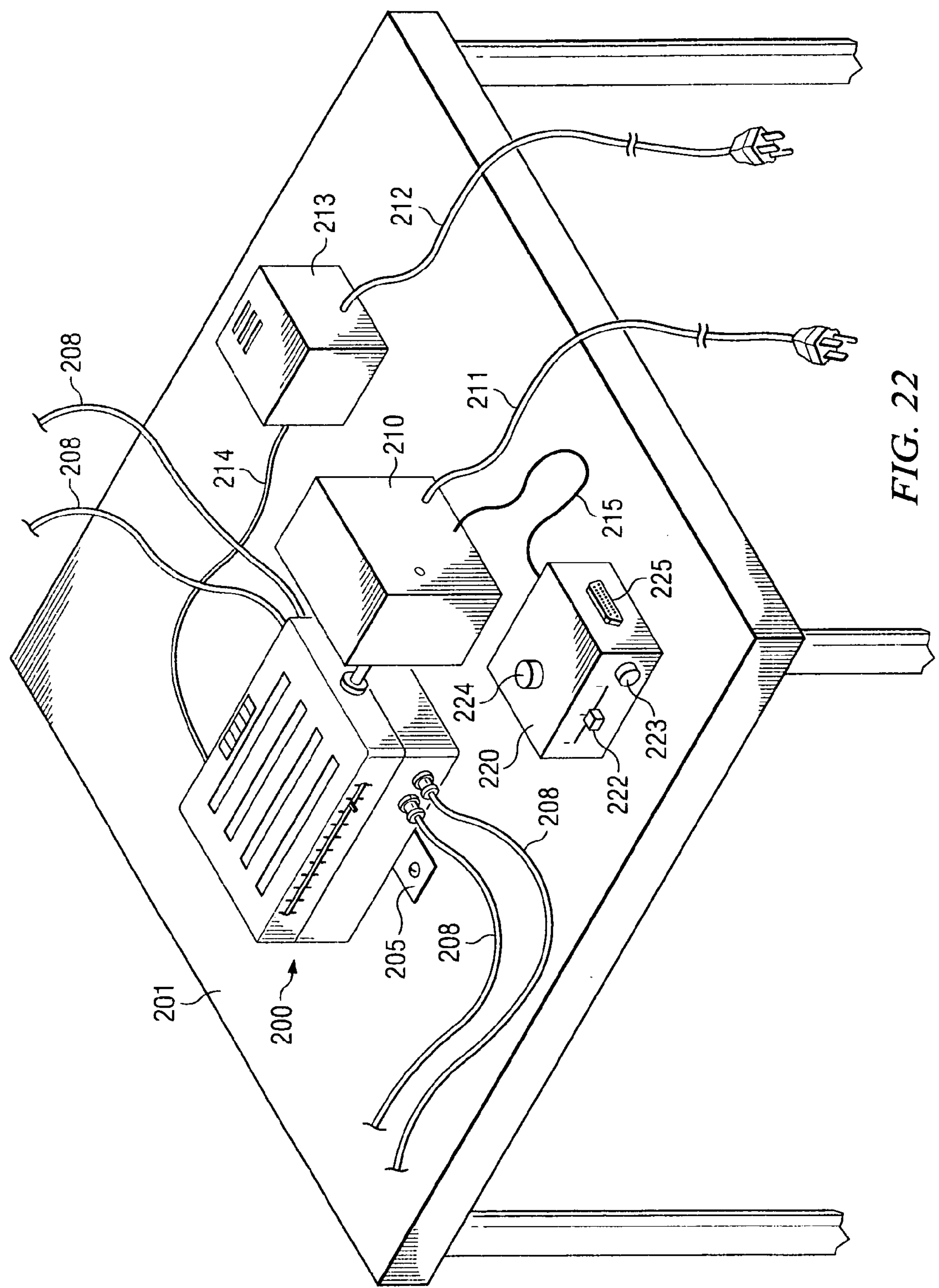
FIG. 22 is a perspective drawing of an exemplary embodiment of the present invention wherein the bone cement dispenser is mounted on a table top.

FIG. 22 is a diagram of an alternative embodiment of the present invention wherein a bone cement dispenser is mounted on a table instead of being held by hand. Furthermore, the alternative embodiment has automatic means for dispensing cement. Bone cement dispenser 200 is mounted onto table 201 by mounting plates 205 attached thereto. Output cement hoses 208 are connected to Luer-lock connectors on the outside of cement dispenser 200 and are appropriately placed in the receiving patient according to required surgical process. Bone cement dispenser 200 has cold and hot plates driven by a Peltier cooling block, the Peltier cooling block requiring DC power supply 213, the electrical input cable 212 to DC power supply 213 being connected to premises AC power and the output DC cable 214 being connected to the Peltier cooling block.

Stepper motor 210 is coupled to bone cement dispenser 200 to actuate a cement dispensing mechanism contained therein, stepper motor 210 having an electrical cable 211 connected to electrical power and electrical control cable 215 connected to motor controller 220. Motor controller 220 may selectably operate with a programmable step size to inject a given amount of cement. Alternatively, motor controller 220 may operate to deliver a continuous programmable flow of cement by continuous stepping to match a curing time and temperature. Motor controller 220 has step button 224 to operate a programmable injection of cement and control means 222 for selecting forward motion to continuously inject cement, for selecting reverse motion to reset cement dispenser 200, and step modes to programmably inject a fixed amount of cement. Motor controller has a step size and velocity selector control 223. Alternatively, motor controller 220 may be interfaced to a computer for more detailed control by computer interface 225.

In another embodiment, electronics integrated into the bone cement dispenser may include a timer, an ambient temperature sensor, temperature sensors on the hot and cold junction surfaces, and a rotary position sensor. A computer may be interfaced to evaluate Arrhenius equation to predict the remaining set up time available, provide visual feedback on the optimal flow rate, calculate the infused volume, and control the Peltier junction temperature.

Another embodiment is conceived to switch the current direction through the Peltier junction plates so as to cool the cement just prior to dispensation, thus decreasing the polymerization prior to dispensation.

In yet another embodiment combining the integrated electronics and the stepper motor and motor controller with computer interface, the computer may further control the dispensation of cement according to optimal flow rate computations and calculated infused volumes.

While these exemplary embodiments have been described along with other illustrative embodiments, this description is not intended to be construed in a limiting sense. Various modifications and combinations of the exemplary and illustrative embodiments, as well as other embodiments, will be apparent to persons skilled in the art upon reference to the description. It is therefore intended that the appended claims encompass any such modifications or embodiments.

What is claimed is:

1. An apparatus for dispensing a temperature sensitive cement during a surgical operation comprising:

a housing having a cement exit port;

a flexible cement packet, within the housing, containing the temperature sensitive cement;

a thermocouple assembly providing a first temperature controlled region and a second temperature controlled region;

the first temperature controlled region being adjacent the flexible cement packet;

the second temperature controlled region being adjacent the cement exit port;

a cement extractor means, adjacent the cement packet, for moving cement out of the flexible cement packet and toward the exit port and, wherein the cement extractor means comprises:

a frame;

a threaded shaft rotationally mounted in the frame;

a circular disk pivotally mounted in the frame adjacent to and engaging the threaded shaft;

the circular disk further comprising a radial slot containing a ball; and a guide means, adjacent the flexible cement packet, for driving the ball along the flexible cement packet when the threaded shaft is turned.

2. The apparatus of claim 1 wherein the thermocouple assembly further comprises:

a first plate having a cavity in ducted communication with a selector dial;

the selector dial adjacent the first plate and adjacent a second plate wherein the selector dial defines an off-center passage in ducted communication with the second plate;

the second plate having a first surface and a second surface, wherein the second plate further includes a set of channels extending from the first surface to the second surface, each of the set of channels in ducted communication with a set of outlet hoses; and, a Peltier junction plate adjacent the first plate and adjacent the second plate and surrounding the selector dial.

3. The apparatus of claim 2 wherein the Peltier junction plate is electronically connected to transfer heat from the first plate to the second plate.

4. The apparatus of claim 2 wherein the Peltier junction plate is electronically connected to transfer heat from the second plate to the first plate.

5. The apparatus of claim 1 wherein the flexible cement packet further comprises a spiral cavity containing the temperature sensitive cement; and the guide means further comprises a ball guide having a spiral groove adjacent the ball and adjacent the spiral cavity;

a cement receiver, adjacent the spiral cavity, having a spiral track;

whereby when the circular disk is turned, the ball is advanced along the spiral groove and the spiral track and forces the temperature sensitive cement out of the spiral cavity toward the exit port.

6. The apparatus of claim 1 wherein the housing further includes an indicator means extending from the housing and adjacent a set of calibrated graticules, for indicating the amount of temperature sensitive cement in the flexible cement packet.

7. The apparatus of claim 1 wherein the housing further includes a color scale adjacent a set of transparent windows, whereby the transparent windows are aligned over the cement packet;

wherein the flexible cement packet contains a transparent region adjacent the temperature sensitive cement; and wherein the temperature sensitive cement includes a colored temperature indicator.

8. The apparatus of claim 1 wherein the cement extractor is manually operated.

9. The apparatus of claim 1 wherein the cement extractor means is advanced by an electric motor controlled by a controller.

10. The apparatus of claim 9 wherein the controller is connected to a computer and the computer is programmed to advance the cement extraction means and to monitor the temperature of the Peltier junction.

11. The apparatus of claim 1 wherein the cement exit port includes a set of alternative exit ports and a set of outlet hoses is connected to the set of alternative exit ports.

12. The apparatus of claim 1 wherein the cement packet is further comprised of:

an upper surface sealed to a lower surface;

a tubular cavity formed between the upper surface and the lower surface which contains the temperature sensitive cement.

13. The apparatus of claim 12 wherein the tubular cavity is preformed in a spiral geometry.

14. The apparatus of claim 1 wherein the temperature sensitive cement is PMMA cement.

15. The apparatus of claim 1 wherein the temperature sensitive cement includes a visual catylization indicator dye.

16. An apparatus for dispensing a temperature sensitive cement during a surgical operation comprising:

a housing having a cement exit port;

a flexible cement packet, within the housing, containing the temperature sensitive cement;

a thermocouple assembly providing a first temperature controlled region and a second temperature controlled region;

the first temperature controlled region being adjacent the flexible cement packet;

the second temperature controlled region being adjacent the cement exit port;

a cement extractor means, adjacent the cement packet, for moving cement out of the flexible cement packet and toward the exit port; and wherein the cement extractor means comprises:

a frame having a first end plate connected to a second end plate by a first guide rail and a second guide rail;

a shaft, having a first set of threads, rotatably mounted in the frame, wherein the shaft is generally parallel to the first guide rod and the second guide rod;

a block, slidably mounted on the first guide rail and the second guide rail;

the block further includes a hole having a second set of threads, wherein the first set of threads engages the second set of threads, whereby the block translates along the shaft when the shaft is rotated in the frame;

a semi-cylindrical protrusion mounted on the block, adjacent the flexible cement packet; and wherein the semi-cylindrical protrusion advances along the flexible cement packet when the block translates along the shaft.

17. The apparatus of claim 16 wherein the thermocouple assembly further comprises:

a first plate having a cavity in ducted communication with a selector dial;

the selector dial adjacent the first plate and adjacent a second plate wherein the selector dial defines an off-center passage in ducted communication with the second plate;

the second plate having a first surface and a second surface, wherein the second plate further includes a set of channels extending from the first surface to the second surface, each of the set of channels in ducted communication with a set of outlet hoses; and, a Peltier junction plate adjacent the first plate and adjacent the second plate and surrounding the selector dial.

18. The apparatus of claim 17 wherein the Peltier junction plate is electronically connected to transfer heat from the first plate to the second plate.

19. The apparatus of claim 17 wherein the Peltier junction plate is electronically connected to transfer heat from the second plate to the first plate.

20. The apparatus of claim 16 wherein the housing further includes an indicator means extending from the housing and adjacent a set of calibrated graticules, for indicating the amount of temperature sensitive cement in the flexible cement packet.

21. The apparatus of claim 16 wherein the housing further includes a color scale adjacent a set of transparent windows, whereby the transparent windows are aligned over the cement packet;

wherein the flexible cement packet contains a transparent region adjacent the temperature sensitive cement; and wherein the temperature sensitive cement includes a colored temperature indicator.

22. The apparatus of claim 16 wherein the cement extractor is manually operated.

23. The apparatus of claim 16 wherein the cement extractor means is advanced by an electric motor controlled by a controller.

24. The apparatus of claim 23 wherein the controller is connected to a computer and the computer is programmed to advance the cement extraction means and to monitor the temperature of the Peltier junction.

25. The apparatus of claim 16 wherein the cement exit port includes a set of alternative exit ports and a set of outlet hoses is connected to the set of alternative exit ports.

26. The apparatus of claim 16 wherein the cement packet is further comprised of:

an upper surface sealed to a lower surface;

a tubular cavity formed between the upper surface and the lower surface which contains the temperature sensitive cement.

27. The apparatus of claim 26 wherein the tubular cavity is preformed in a linear geometry.

28. The apparatus of claim 16 wherein the temperature sensitive cement is PMMA cement.

29. The apparatus of claim 16 wherein the temperature sensitive cement includes a visual catylization indicator dye.

30. The apparatus of claim 16 wherein the cement extractor means further comprises:

a rod, having a cylindrical roller slidably mounted thereon, and adjacent the flexible cement packet connected to the block;

a selector attached to the cylindrical roller and slidably mounted on the rod, whereby the selector extends through the housing.

31. The apparatus of claim 16 wherein the thermocouple further comprises:

an array of individual hot plates adjacent an array of individual Peltier junction plates, wherein each individual Peltier junction plate is thermally insulated from each other individual Peltier junction plate;

an array of individual cold plates, each having a first end and a second end, adjacent the array of Peltier junction plates; and wherein the flexible cement packet is comprised of a set of individual cement packets, where each individual cement packet is adjacent each individual cold plate.

* * * * *